(12) United States Patent
Zhu et al.

(10) Patent No.: US 10,155,721 B2
(45) Date of Patent: Dec. 18, 2018

(54) LIGNANAMIDES AND A METHOD OF TREATING NEURODEGENERATIVE DISEASES BY USING THE SAME

(71) Applicant: Macau University of Science and Technology, Macau (CN)

(72) Inventors: Guo-Yuan Zhu, Macau (CN); Zhi-Hong Jiang, Macau (CN); Ji Yang, Macau (CN); Xiao-Jun Yao, Macau (CN); Xin Liu, Macau (CN); Jing Fu, Macau (CN); Li-Ping Bai, Macau (CN); Liang Liu, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 15/495,949

(22) Filed: Apr. 24, 2017

(65) Prior Publication Data

US 2018/0305300 A1  Oct. 25, 2018

(51) Int. Cl.
   *C07C 237/26*  (2006.01)
   *C07C 231/24*  (2006.01)

(52) U.S. Cl.
   CPC .......... *C07C 237/26* (2013.01); *C07C 231/24* (2013.01)

(58) Field of Classification Search
   CPC .... C07C 237/26; C07C 231/24; C07C 67/313
   See application file for complete search history.

(56) References Cited

PUBLICATIONS

Van (Journal of Agricultural and Food Chemistry, 63, 2015, 10611-10619).*
Yan (Journal of Agricultural and Food Chemistry; 2015, 63, 10611-10619).*
Malhotra (Proceedings of the National Academy of Sciences 2008, 105, 47, 18525-18530).*
Zias J., Stark, H., Sellgman, J., Levy, R., Werker, E., Breuer, A., and Mechoulam, R., Early medical use of cannabis, Nature, vol. 363, No. 6426, pp. 215, 1993.
Oomah, B. D., Busson, M., Godfrey, D. V., and Drover, J. C., Characteristics of hemp (*Cannabis sativa* L) seed oil, Food chemistry, vol. 76, No. 1, pp. 33-43, 2002.
Ahmed, S. A., Ross, S. A, Slade, D., Radwan, M. M., Zulfiqar, F., and Elsohly, M. A., Cannabinoid ester constituents from high-potency Cannabis sativa, Journal of natural products, vol. 71, No. 4, pp. 536-542, 2008.
Montserrat-De La Paz, S., Marín-Aguilar, F., García-Giménez, M. D., and Fernández-Arche, M. A, Hemp (*Cannabis sativa* L.) seed oil: analytical and phytochemical characterization of the unsaponifiable fraction, Journal of agricultural and food chemistry, vol. 62, No. 5, pp. 1105-1110, 2014.
Jiang, H. E., Li, X., Zhao, Y. X., Ferguson, D. K., Hueber, F., Bera, S., Wang, Y. F., Zhao, L C., Liu, C. J., and Li, C. S., A new insight into *Cannabis sativa* (Cannabaceae) utilization from 2500-year-old Yanghai Tombs, Xinjiang, China, Journal of Ethnopharmacology, vol. 108, No. 3, pp. 414-422, 2006.
Richard, M. N., Ganguly, R., Steigerwald, S. N., Al-Khalifa, A., and Pierce, G. N., Dietary hempseed reduces platelet aggregation1, Journal of Thrombosis and Haemostasis, vol. 5, No. 2, pp. 424-425, 2007.
Prociuk, M. A., Edel, A. L., Richard, M. N., Gavel, N. T., Ander, B. P., Dupasquier, C. M. C., and Pierce, G. N., Cholesterol-induced stimulation of platelet aggregation is prevented by a hempseed-enriched diet, Canadian journal of physiology and pharmacology, vol. 86, No. 4, pp. 153-159, 2008.
Cheng, C. W., Bian, Z. X., Zhu, L. X., Wu, J. C., and Sung, J. J., Efficacy of a Chinese herbal proprietary medicine (Hemp Seed Pill) for functional constipation, The American journal of gastroenterology, vol. 106, No. 1, pp. 120-129, 2011.
Schwab, U. S., Callaway, J. C., Erkkilä, A. T., Gynther, J., Uusitupa, M. I., and Järvinen, T., Effects of hempseed and flaxseed oils on the profile of serum lipids, serum total and lipoprotein lipid concentrations and haemostatic factors, European journal of nutrition, vol. 45, No. 8, pp. 470-477, 2006.
Al-Khalifa, A., Maddaford, T. G., Chahine, M. N., Austria, J. A., Edel, A. L., Richard, M. N., Ander, B. P., Gavel, N., Kopilas, M., Ganguly, R., Ganguly, P.K., and Pierce, G.N., Effect of dietary hempseed intake on cardiac ischemia-reperfusion injury, American Journal of Physiology-Regulatory, Integrative and Comparative Physiology, vol. 292, No. 3, pp. R1198-R1203, 2007.

(Continued)

*Primary Examiner* — Pancham Bakshi
(74) *Attorney, Agent, or Firm* — Eagle IP Limited; Jacqueline C. Lui

(57) ABSTRACT

One example embodiment is a lignanamide that includes a benzo-angular triquinane skeleton. The lignanamide is represented by formula (I) and any derivative of the formula (I), in which R is represented by —OH or —OCH3. Another example embodiment relates to a method of treating neurodegenerative disease by administering the lignanamide of the formula (I) to a person in need thereof.

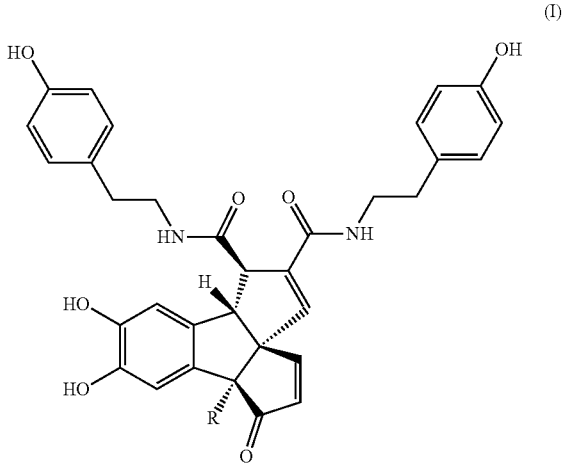

(I)

4 Claims, 38 Drawing Sheets
(32 of 38 Drawing Sheet(s) Filed in Color)

(56) References Cited

PUBLICATIONS

Luo, J., Yin, J. H., Wu, H. Z., and Wei, Q., Extract from Fructus cannabis activating calcineurin improved learning and memory in mice with chemical drug-induced dysmnesia, Acta Pharmacologica Sinica, vol. 24, No. 11, pp. 1137-1142, 2003.

Andre, C. M., Hausman, J. F., and Guerriero, G., Cannabis sativa: the plant of the thousand and one molecules, Frontiers in plant science, vol. 7, No. 19, pp. 1-17, 2016.

Holler, J. M., Bosy, T. Z., Dunkley, C. S., Levine, B., Past, M. R., and Jacobs, A., Delta9-tetrahydrocannabinol content of commercially available hemp products, Journal of analytical toxicology, vol. 32, No. 6, pp. 428-432, 2008.

Chang, C. W., Tung, C. W., Tsai, C. C., Wu, Y. T., and Hsu, M. C., Determination of cannabinoids in hemp nut products in Taiwan by HPLC-MS/MS coupled with chemometric analysis: quality evaluation and a pilot human study, Drug testing and analysis, vol. 9, No. 6, pp. 888-897, 2017.

Sakakibara, I., Katsuhara, T., Ikeya, Y., Hayashi, K., and Mitsuhashi, H., Cannabisin A, an arylnaphthalene lignanamide from fruits of Cannabis sativa, Phytochemistry, vol. 30, No. 9, pp. 3013-3016, 1991.

Sakakibara, I., Ikeya, Y., Hayashi, K., and Mitsuhashi, H., Three phenyldihydronaphthalene lignanamides from fruits of Cannabis sativa, Phytochemistry, vol. 31, No. 9, pp. 3219-3223, 1992.

Sakakibara, I., Ikeya, Y., Hayashi, K., Okada, M., and Maruno, M., Three acyclic bis-phenylpropane lignanamides from fruits of Cannabis sativa, Phytochemistry, vol. 38, No. 4, pp. 1003-1007, 1995.

Lesma, G., Consonni, R., Gambaro, V., Remuzzi, C., Roda, G., Silvani, A., Vece, V., and Visconti, G. L., Cannabinoid-free *Cannabis sativa* L. grown in the Po valley: evaluation of fatty acid profile, antioxidant capacity and metabolic content. Natural product research, vol. 28, No. 21, pp. 1801-1807, 2014.

Yan, X., Tang, J., Dos Santos Passos, C., Nurisso, A, Simöes-Pires, C. A., Ji, M., Lou, P., & Fan, P., Characterization of lignanamides from hemp (*Cannabis sativa* L) seed and their antioxidant and acetylcholinesterase inhibitory activities, Journal of Agricultural and Food Chemistry, vol. 63,No. 49, pp. 10611-10619, 2015.

Chen, T., He, J., Zhang, J., Li, X., Zhang, H., Hao, J., and Li, L., The isolation and identification of two compounds with predominant radical scavenging activity in hempseed (seed of *Cannabis sativa* L.), Food chemistry, vol. 134, No. 2, pp. 1030-1037, 2012.

Chen, T., Hao, J., He, J., Zhang, J., Li, Y., Liu, R., and Li, L., Cannabisin B induces autophagic cell death by inhibiting the AKT/mTOR pathway and S phase cell cycle arrest in HepG2 cells, Food chemistry, vol. 138, No. 2, pp. 1034-1041, 2013.

Zhu, G. Y., Yao, X. J., Liu, L., Bai, L. P., and Jiang, Z. H., Alistonitrine A, a caged monoterpene indole alkaloid from Alstonia scholaris, Organic letters, vol. 16, No. 4, pp. 1080-1083, 2014.

Hetz, C., and Mollereau, B., Disturbance of endoplasmic reticulum proteostasis in neurodegenerative diseases, Nature Reviews Neuroscience, vol. 15, No. 4, pp. 233-249, 2014.

Hetz, C., Chevet, E., and Oakes, S. A., Proteostasis control by the unfolded protein response, Nature cell biology, vol. 17, No. 7, pp. 829-838, 2015.

Freeman, O. J., and Mallucci, G. R., The UPR and synaptic dysfunction in neurodegeneration, Brain research, vol. 1648, pp. 530-537, 2016.

Zhu, G. Y., Li, Y. W., Tse, A. K. W., Hau, D. K. P., Leung, C. H., Yu, Z. L., and Fong, W. F., 20 (S)-Protopanaxadiol, a metabolite of ginsenosides, induced cell apoptosis through endoplasmic reticulum stress in human hepatocarcinoma HepG2 cells, European journal of pharmacology, vol. 668, No. 1, pp. 88-98, 2011.

Zhu, G. Y., Wong, B. C. K., Lu, A., Bian, Z. X., Zhang, G., Chen, H. B.,Wong, Y.F., Fong, W.F., and Yang, Z., Alkylphenols from the roots of Ardisia brevicaulis induce G1 arrest and apoptosis through endoplasmic reticulum stress pathway in human non-small-cell lung cancer cells, Chemical and Pharmaceutical Bulletin, vol. 60, No. 8, pp. 1029-1036, 2012.

Jaquette, L. A., and Geng, F., A highly abbreviated synthesis of pentalenene by means of the squarate ester cascade, Organic letters, vol. 4, No. 25, pp. 4547-4549, 2002.

Pallerla, M. K., and Fox, J. M., Enantioselective synthesis of (−)-Pentalenene, Organic letters, vol. 9, No. 26, pp. 5625-5628, 2007.

Srikrishna, A., and Gowri, V., Enantiospecific synthesis of angular triquinanes, Tetrahedron: Asymmetry, vol. 22, No. 14, pp. 1553-1559, 2011.

Quaderer, R., Omura, S., Ikeda, H., and Cane, D. E., Pentalenolactone biosynthesis. Molecular cloning and assignment of biochemical function to Ptll, a cytochrome P450 of *Streptomyces avermitilis*, Journal of the American Chemical Society, vol. 128, No. 40, 13036-13037, 2006.

Srikrishna, A., Nagaraju, G., and Sheth, V. M., Enantiospecific first total synthesis of (6S, 7R)-silphiperfolan-6-ol, Tetrahedron, vol. 68, No. 12, pp. 2650-2656, 2012.

Kim, Y. J., Yoon, Y., and Lee, H. Y., An asymmetric total synthesis of (+)-pentalenene, Tetrahedron, vol. 69, No. 36, pp. 7810-7816, 2013.

\* cited by examiner

Figure 1A                    Figure 1B

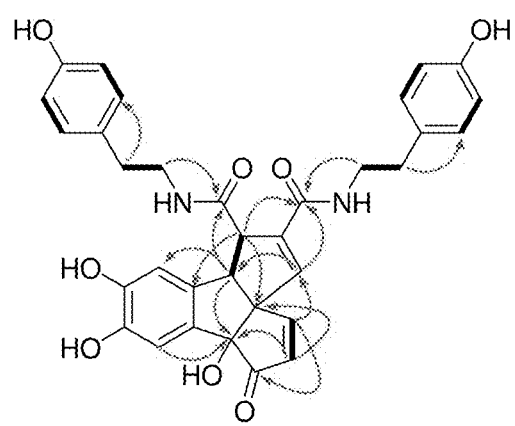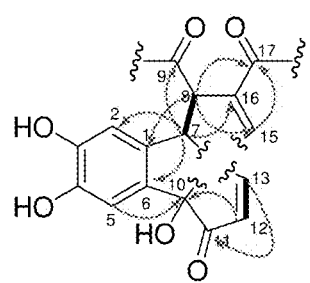
HMBC
$^1H$-$^1H$ COSY
Figure 4A							Figure 4B

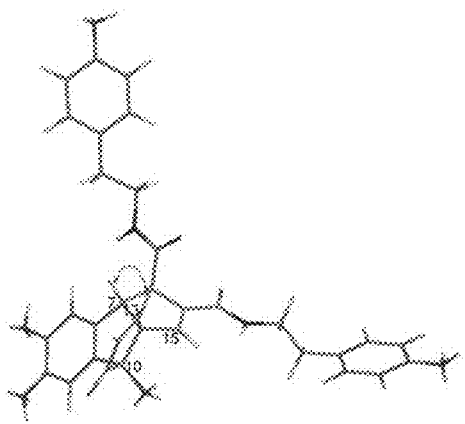 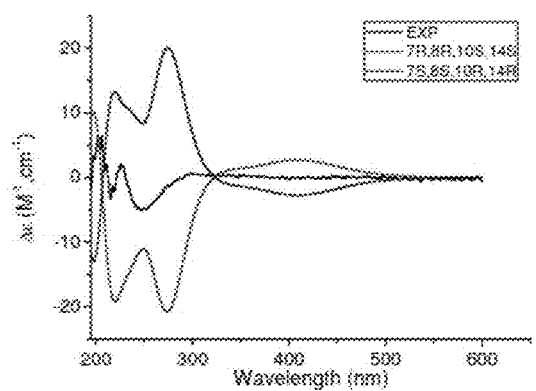
Figure 5                    Figure 6

700

| Sativamide B |
|---|
| $[\alpha]^{25}_D$ −7.8 (c = 1, MeOH) |
| UV (MeOH) $\lambda_{max}$ (log ε) 283 (3.77), 224 (4.56) nm |
| IR (KBr) $v_{max}$ 3418, 2934, 2361, 1709, 1650, 1613, 1543, 1515, 1456, 1383, 1317, 1245, 1108, 1046, 829, 783, 669, 559, 480 cm$^{-1}$ |
| HRESIMS m/z 597.2240 [M + H]$^+$ (calcd for $C_{34}H_{33}N_2O_8$, 597.2231), 619.2059 [M + Na]$^+$ (calcd for $C_{34}H_{32}N_2O_8Na$, 619.2051) |

Figure 7

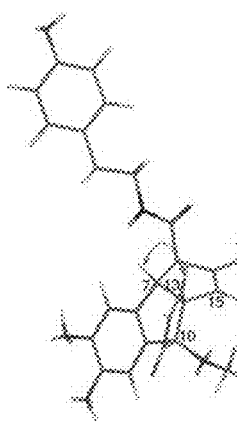
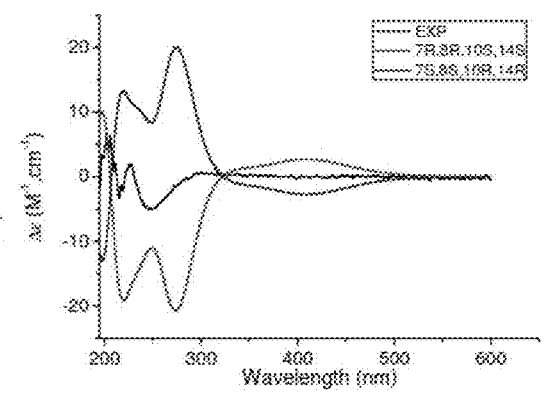
Figure 9                    Figure 10

Figure 12A
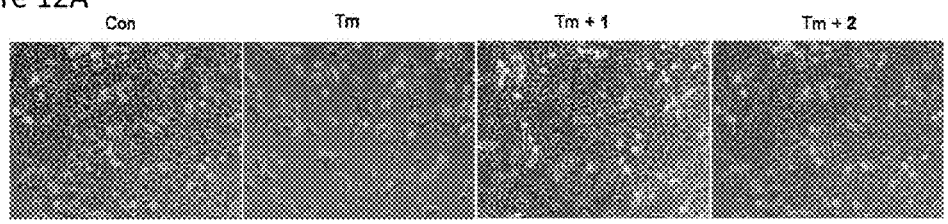
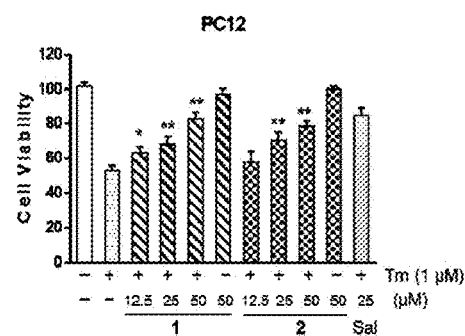
Figure 12B
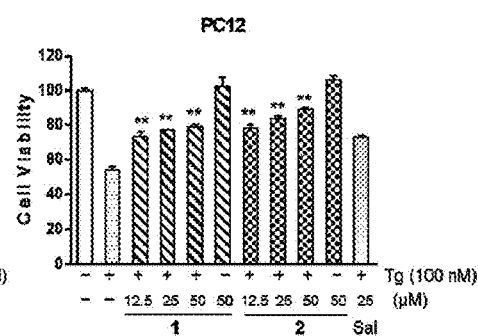
Figure 12C

Figure 13A
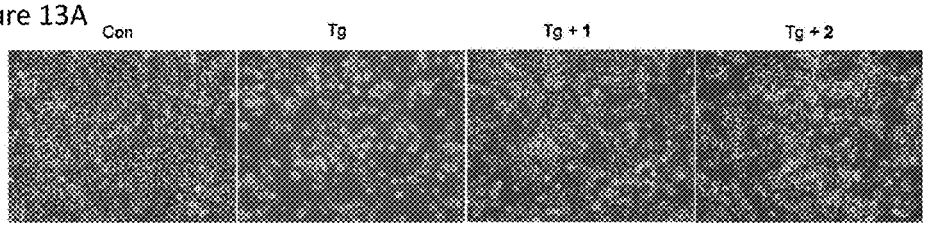
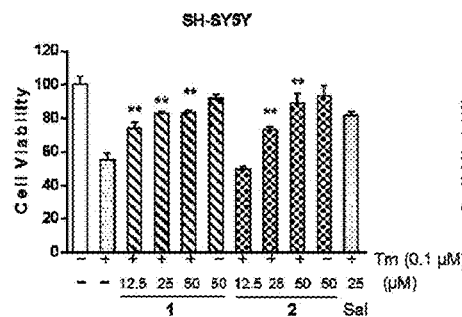
Figure 13B
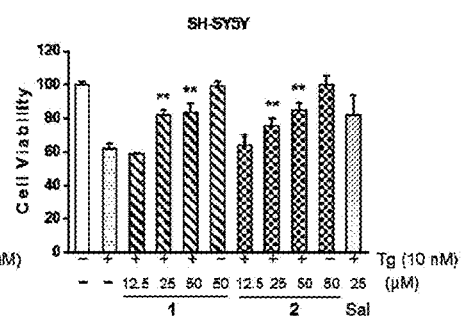
Figure 13C

LIGNANAMIDES AND A METHOD OF TREATING NEURODEGENERATIVE DISEASES BY USING THE SAME

FIELD OF THE INVENTION

The present invention relates to a lignanamide and a method to treat neurodegenerative disease by using the lignanamide.

BACKGROUND

*Cannabis sativa* L. is cultivated worldwide and used as food, fiber, and medicine. Metabolites isolated from *Cannabis sativa* L. are used in drug discovery for treating neurodegenerative disorders.

In view of the demand for effectively treating neurodegenerative disorders, improvements in method that isolate metabolites from *Cannabis sativa* L., which can be used to treat neurodegenerative disorders, are desired.

SUMMARY OF THE INVENTION

One example embodiment is a lignanamide that includes a benzo-angular triquinane skeleton. The lignanamide is represented by formula (I) and any derivative of the formula (I), in which R is represented by —OH or —OCH3.

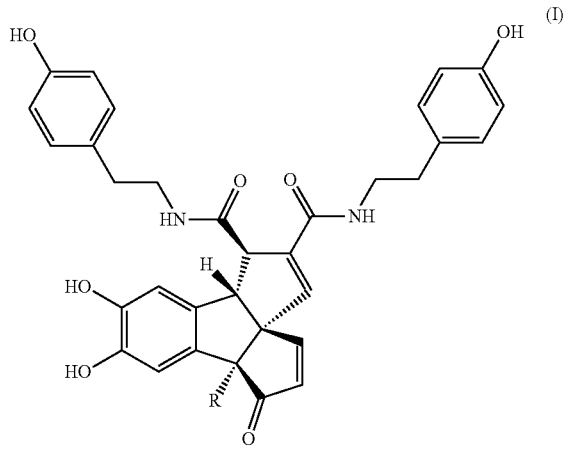

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A and 4B show heteronuclear multiple bond correlation (HMBC) correlations and $^1$H-$^1$H correlation spectroscopy (COSY) correlation of Sativamide A in accordance with an example embodiment.

FIG. 5 shows nuclear overhauser effect spectroscopy (NOESY) correlation of Sativamide A in accordance with an example embodiment.

FIG. 6 shows electronic circular dichroism (ECD) curves of Sativamide A in accordance with an example embodiment.

FIG. 7 shows a table that provides physico-chemical constants of Sativamide B in accordance with an example embodiment.

FIG. 9 shows NOESY correlation of Sativamide B in accordance with an example embodiment.

FIG. 10 shows ECD curves of Sativamide B in accordance with an example embodiment.

FIG. 12A shows microscopic observations (with magnification of 20×) of PC12 cells that are pre-treated with Sativamide A and Sativamide B in accordance with an example embodiment.

FIGS. 12B and 12C show results of thiazolyl blue tetrazolium bromide (MTT) assays on tunicamycin (Tm)-induced cytotoxicity and thapsigargin (Tg)-induced cytotoxicity in PC12 cells, respectively, in accordance with an example embodiment.

FIG. 13A shows microscopic observations (with magnification of 20×) of SH-SY5Y cells that are pre-treated with Sativamide A and Sativamide B in accordance with an example embodiment.

FIGS. 13B and 13C show results of MTT assays on Tm-induced cytotoxicity and Tg-induced cytotoxicity in SH-SY5Y cells, respectively, in accordance with an example embodiment.

DETAILED DESCRIPTION

Figure 1:
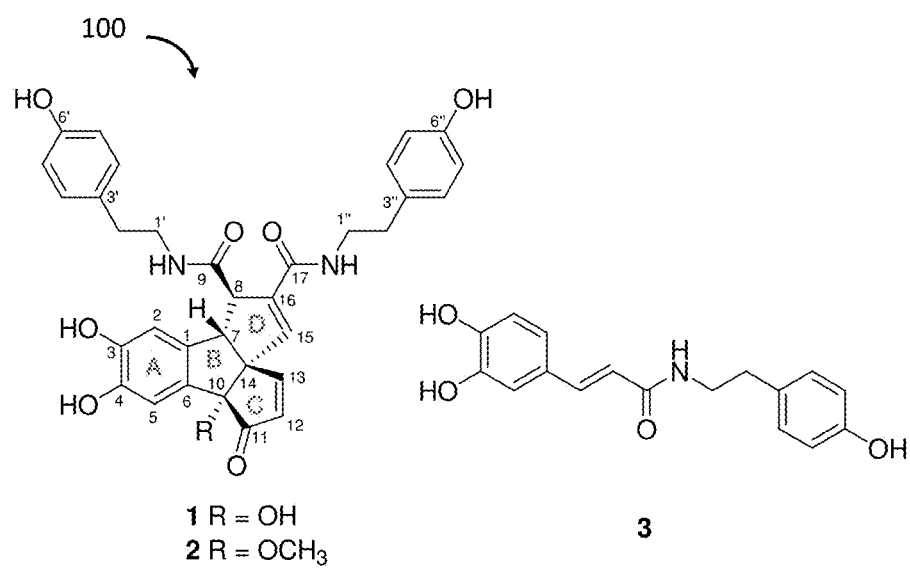
FIGS. 1A and 1B shows Compounds 1-3 in accordance with an example embodiment.

Example embodiments relate to two lignanamides and a method that treats neurodegenerative disease by using a therapeutically effective amount of these lignanamides.

An example embodiment includes a method of treating neurodegenerative disease in a person in need thereof that includes administering a therapeutically effective amount of a lignanamide to the person to treat the neurodegenerative disease. The lignanamide includes a benzo-angular triquinane skeleton. By way of example, the lignanamide is represented by formula (I) and any derivative of the formula (I), in which R is represented by —OH or —OCH3.

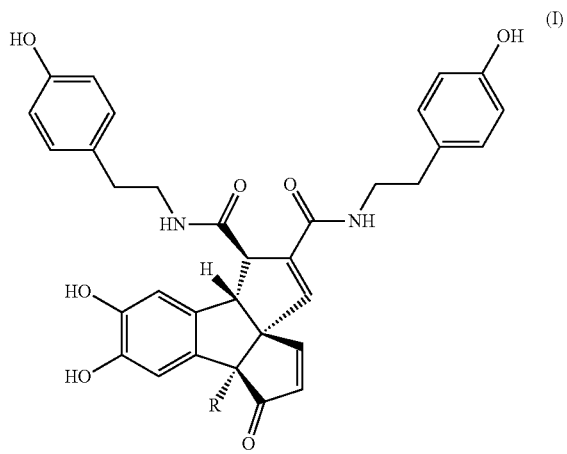

(I)

In one example embodiment, the derivative of the formula (I) includes, but is not limited to, an isomer of the formula (I).

By way of example, the neurodegenerative disease includes neuroblastoma, Parkinson's disease, Alzheimer's disease, pheochromocytoma, Parkinson's disease (PD), Alzheimer's disease (AD), Huntington's disease (HD), and the rarer prion diseases.

In one example embodiment, a method that synthesizes Sativamide A as represented by formula (II) is provided.

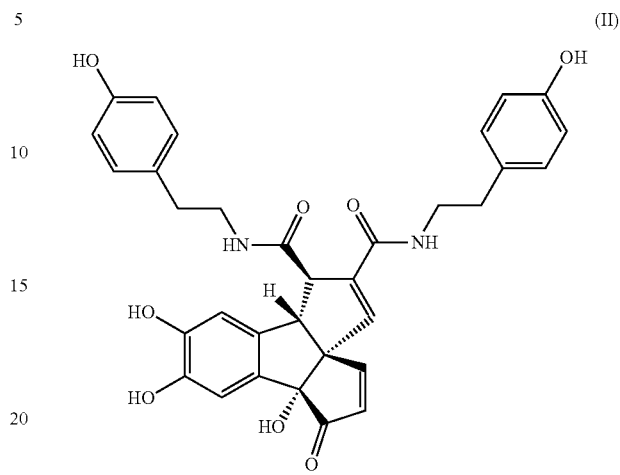

(II)

The method includes isolating N-trans-caffeoyltyramine from *Cannabis sativa*, dimerizing the N-trans-caffeoyltyramine to form a N-trans-caffeoyltyramine dimer, oxidizing the N-trans-caffeoyltyramine dimer to form a hydroxyquinone derivative, decarbonylating the hydroxyquinone derivative to form a decarbonylated hydroxyquinone derivative, and crystallizing the decarbonylated hydroxyquinone derivative to obtain the Sativamide A. By way of example, the Sativamide A is the lignanamide as represented by the formula (I), in which R is represented by —OH. In another example, the Sativamide A is represented by a chemical formula of $C_{33}H_{30}N_2O_8$.

*Cannabis sativa* L. (*C. sativa* L. or *C. sativa*) of the Cannabaceae family, an annual herbaceous plant, is native of western and central Asia and cultivated commercially all over the world. It is used as food, fiber and medicine. *C. sativa* L. is recognized as a highly variable species in the *Cannabis* genus. Two major varieties of *C. sativa* are marijuana (drug type) and hemp (nondrug type). Marijuana has psychoactivity because of the existence of high content of $\Delta^9$-tetrahydrocannabinol (THC), in which the content ranges from 1 to 20%, and is prohibited worldwide. Hemp, with low THC content (<0.3%) and no psychoactive property, is an important industrial source of fiber and food with a global market for its products valued at $100-2000 million annually. In China, the fruits of *C. sativa* (hemp seed) is used as food and traditional Chinese medicine. Hemp seed possesses a wide range of biological activities including anti-platelet aggregation, alleviating functional constipation, lowering cholesterol, cardioprotective effects, and improving learning and memory function.

Cannabinoids, a class of C21 meroterpenoids with psychoactivity, are a specific group of compounds found in *C. sativa*. However, the THC content in hemp seed is usually less than 1 ppm. Lignanamides are the major secondary metabolites isolated from hemp seed, and twenty one lignanamides are isolated from hemp seed. These lignanamides exhibit various bioactivities such as antioxidant, inducing autophagic cell death, inhibiting acetylcholinesterase, and anti-inflammation.

In one example embodiment, two new lignanamides, namely Sativamide A and Sativamide B, are isolated from the hemp seed. By way of example, the Sativamide A and the Sativamide B possess a 6/5/5/5 tetracyclic rearranged nor-lignan carbon skeleton and demonstrate potential neuroprotective activity on various cell models In one example embodiment, the two nor-lignanamides (i.e. Sativamide A and Sativamide B) with an unprecedented skeleton are discovered from hemp seed. The Sativamide A and the Sativamide B represent the first examples of 17-carbon skeleton nor-lignanamides with a unique benzo-angular triquinane ring system. All of the natural angular triquinanes belong to sesquiterpenoids. A great attention of synthetic chemistry community has been drawn to these angular triquinanes because of their highly congested structural features as well as the biosynthetic precursor of an antibiotic drug, pentalenolactone. In another example embodiment, the Sativamide A and the Sativamide B have neuroprotective activity in cells that has undergone ER stress, indicating that the Sativamide A and the Sativamide B can be used in drug discovery of neurodegenerative diseases.

An example embodiment describes experimental procedures in analyzing the Sativamide A and the Sativamide B. Optical rotations are obtained on a Rudolph Research Analytical Autopol I automatic polarimeter (Na 589 nm). Ultraviolet (UV) and circular dichroism (CD) spectra are recorded on a JASCO J-1500 Circular Dichroism Spectrometer. Infrared (IR) spectra are determined on an Agilent Cary 600 series Fourier transform infrared (FT-IR) spectrometer (KBr). Nuclear magnetic resonance (NMR) spectra are recorded on a Bruker Ascend 600 NMR spectrometer (600 MHz for $^1$H and 150 MHz for $^{13}$C) using standard Bruker pulse programs. Samples are dissolved in $CD_3OD$ and the NMR spectra are recorded using the signals of $CD_3OD$ ($^1$H, δ 3.31; $^{13}$C, δ 49.0) as an internal reference. High resolution-electrospray ionization-mass spectroscopy (HR-ESI-MS) spectra are measured on an Agilent 6230 Accurate-Mass Time-of-flight liquid chromatography/mass spectroscopy (TOF-LC/MS) system. Ultra-high performance liquid chromatography (UHPLC) analyses are carried out on an Agilent 1290 Infinity LC system using an Extend-C18 column (1.8 μm, 50×2.1 mm, i.d., Agilent). Semi-preparative high performance liquid chromatography (HPLC) is conducted on the Waters 1525 HPLC system using Grace Alltech Alltima C18 (10 μm, 250×10 mm, i.d.) and Waters XBridge C18 (5 μm, 250×10 mm, i.d.) columns with gradient solvent system composed of $H_2O$ and $CH_3CN$ or MeOH, and with a flow rate of 3.0 mL/min. Medium pressure liquid chromatography (MPLC) is conducted on the Sepacore Flash Chromatography System (Buchi, Switzerland) using a Siliabond® $C_{18}$ ODS column (40-63 μm, 460×36 mm, i.d., Silicycle, Canada). Column chromatography (CC) is carried out with silica gel (40-63 μm, Grace, USA) as packing material. All solvents are of spectroscopic grade or HLPC grade and purchased from Labscan Asia (Bangkok, Thailand) or distilled prior to use.

In one example embodiment, the fruits of *Cannabis sativa* are collected from Linzhou, Henan Province, China. The species are identified by Dr. Zhu G. Y. A voucher specimen (CS-2011510) is deposited at the State Key Laboratory of Quality Research in Chinese Medicine, Macau University of Science and Technology.

An example embodiment describes an extraction method of *C. sativa* to obtain the Sativamide A and the Sativamide B. Air-dried and powdered fruits of *C. sativa* (9.0 kg) are extracted with 80% ethanol (EtOH) (40 L×3) under reflux condition. The combined extracts are concentrated under a reduced pressure to afford a brown residue. The brown residue is suspended in water ($H_2O$) (8 L) and sequentially partitioned with petroleum ether, ethyl acetate (EtOAc) and n-butanol (n-BuOH). The EtOAc-soluble extracts (98 g) are subjected to column chromatography over silica gel eluting with petroleum ether-acetone-methanol (MeOH) gradient (10:1:0→0:5:5, v/v) to result in 36 fractions (Fr.1-Fr.36). Lignanamides are identified as the most abundant compounds in the fractions Fr.25-Fr.35 by liquid chromatography-mass spectroscopy (LC-MS) analysis. Fractions Fr. 28 and Fr.29 are repeatedly purified by MPLC and preparative HPLC to obtain Compound 1 and Compound 2 as shown in FIG. 1A. Fraction Fr. 26 is repeatedly purified by MPLC and preparative HPLC to obtain Compound 3 as shown in FIG. 1B. In one example embodiment, when a R group of a formula 100 as shown in FIG. 1A is a —OH group, the resulting compound is the Sativamide A (i.e. Compound 1). In another example embodiment, when the R group of the formula 100 as shown in FIG. 1A is a $—OCH_3$ group, the resulting compound is the Sativamide B (i.e. Compound 2).

In an example embodiment as shown in FIG. 1A, ring A is a benzene ring that includes carbons C-1 to C-6. Ring B, ring C and ring D form an angular triquinane in which the ring B includes carbons C-1, C-6, C-7, C-10 and C-14, the ring C includes carbons C-10-C-14, and the ring D includes carbon C-7, C-8, C-14, C-15 and C-16.

In one example embodiment, fraction Fr.28 (6 g) is isolated by MPLC with a reversed-phase RP-18 column eluting with a MeOH—$H_2O$ gradient (20:80→80:20, v/v), and further repeatedly purified by preparative HPLC eluting with an acetonitrile (MeCN)—$H_2O$ gradient (30:70, 25:75, v/v) to yield the Compound 2 as shown in FIG. 1A (with a mass of 7 mg).

In one example embodiment, fraction Fr.29 (with a mass of 15 g) is re-subjected by CC to a silica gel column chromatography eluting with a chloroform ($CHCl_3$)-MeOH gradient (20:1→4:1, v/v) to yield 20 subfractions (Fr.29.1-Fr.29.20). Subfraction Fr.29.13 is isolated by MPLC with a reversed-phase RP-18 column eluting with a MeOH—$H_2O$ gradient (20:80→100:0, v/v), and further repeatedly purified by preparative HPLC eluting with a MeCN—$H_2O$ gradient (26:74, v/v) to yield the Compound 1 as shown in FIG. 1A (with a mass of 22 mg).

In one example embodiment, fraction Fr.26 (5 g) is isolated by MPLC with a reversed-phase RP-18 column eluting with a MeOH—H2O gradient (20:80→80:20, v/v) to yield the Compound 3 as shown in FIG. 1A (120 mg).

Figure 2:
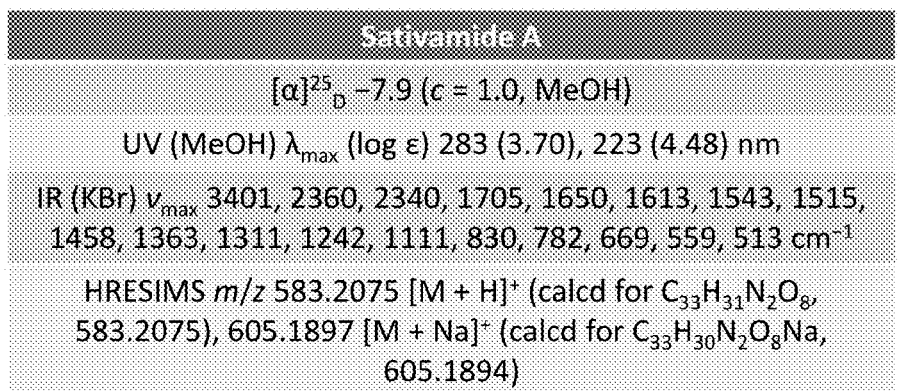
FIG. 2 shows a table that provides physico-chemical constants of Sativamide A in accordance with an example embodiment.
Figure 16:
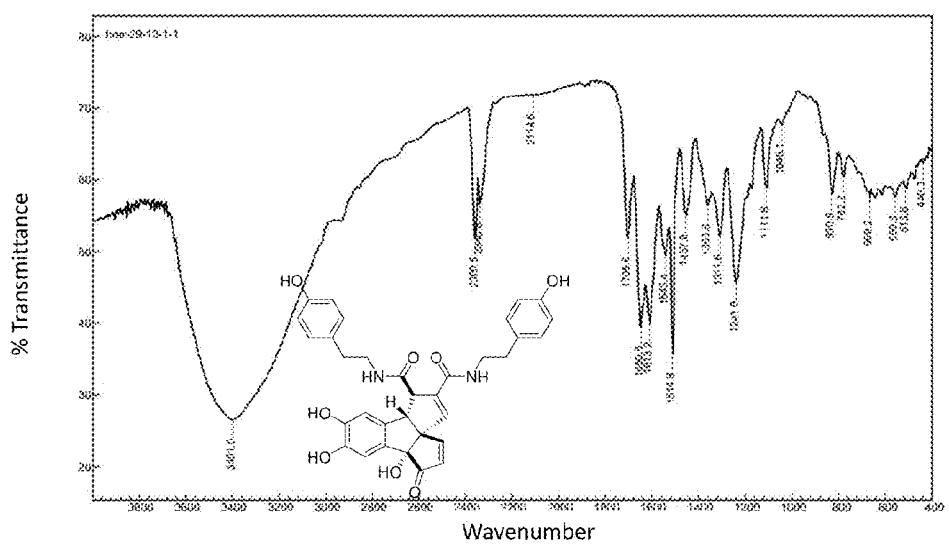
FIG. 16 shows an infrared (IR) (KBr) spectrum of Sativamide A in accordance with an example embodiment.
Figure 17:
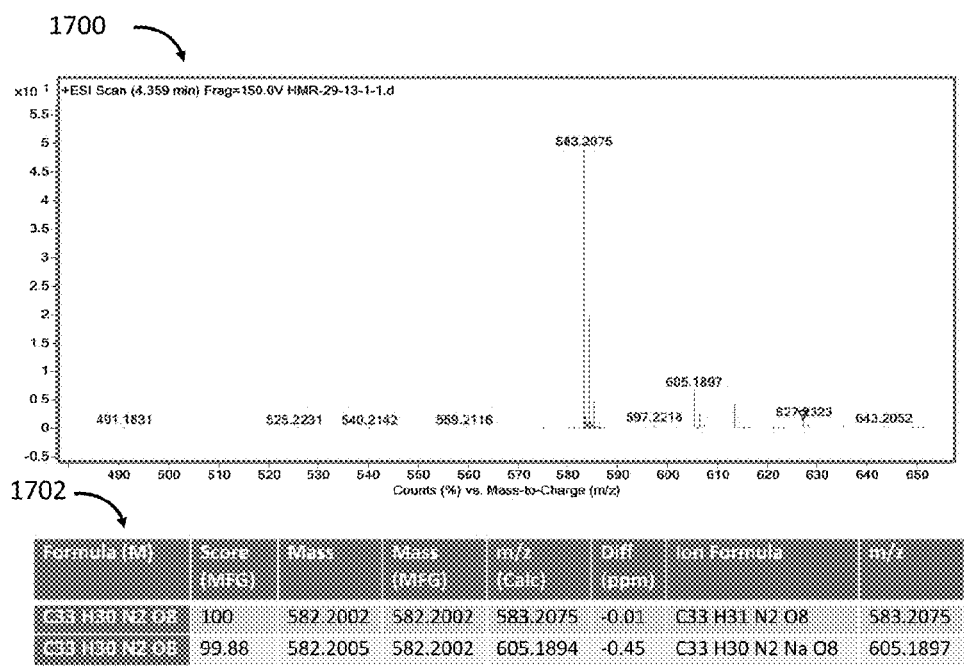
FIG. 17 shows a high resolution electrospray ionization mass spectroscopy (HR-ESI-MS) spectrum of Sativamide A in accordance with an example embodiment.

In one example embodiment, the Sativamide A is obtained as a light yellow powder. By way of example, Table 200 in FIG. 2 shows physico-chemical constants of the Sativamide A. Its molecular formula is established as $C_{33}H_{30}N_2O_8$ on the basis of HR-ESI-MS analysis (m/z 583.2075 [M+H]$^+$, (calcd for $C_{33}H_{31}N_2O_8$, 583.2075), indicating that the Sativamide A has 20 degrees of unsaturation. FIG. 17 shows a HR-ESI-MS spectrum 1700 of the Sativamide A. Table 1702 shows the HR-ESI-MS data of the Sativamide A. FIG. 16 shows an infrared (IR) spectrum of the Sativamide A that displays strong absorptions at 1705, 1650 and 1613 cm$^{-1}$ that suggests a presence of carbonyl groups.

Figure 14:
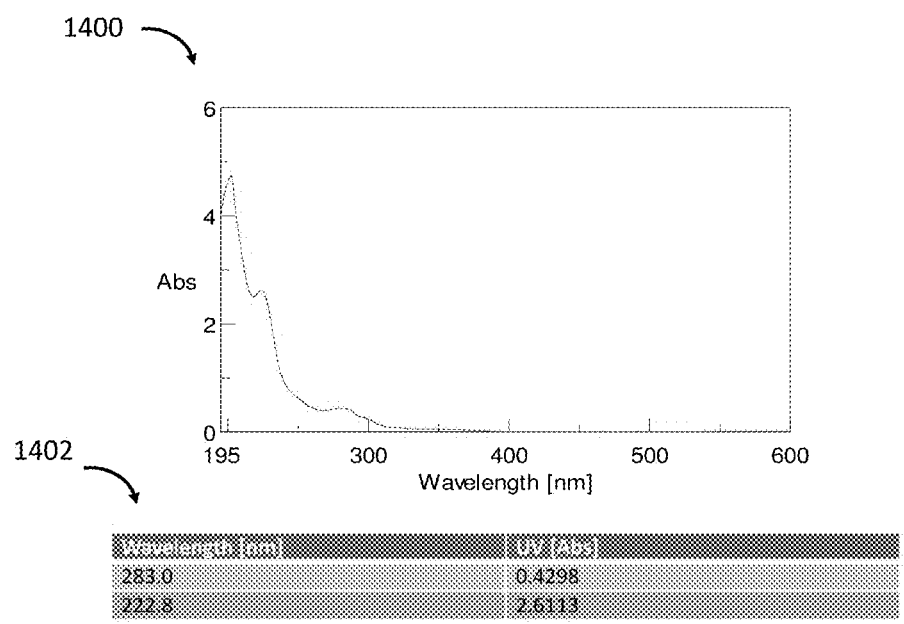
FIG. 14 shows an ultraviolet (UV) spectrum of Sativamide A in CH$_3$OH in accordance with an example embodiment.
Figure 15:
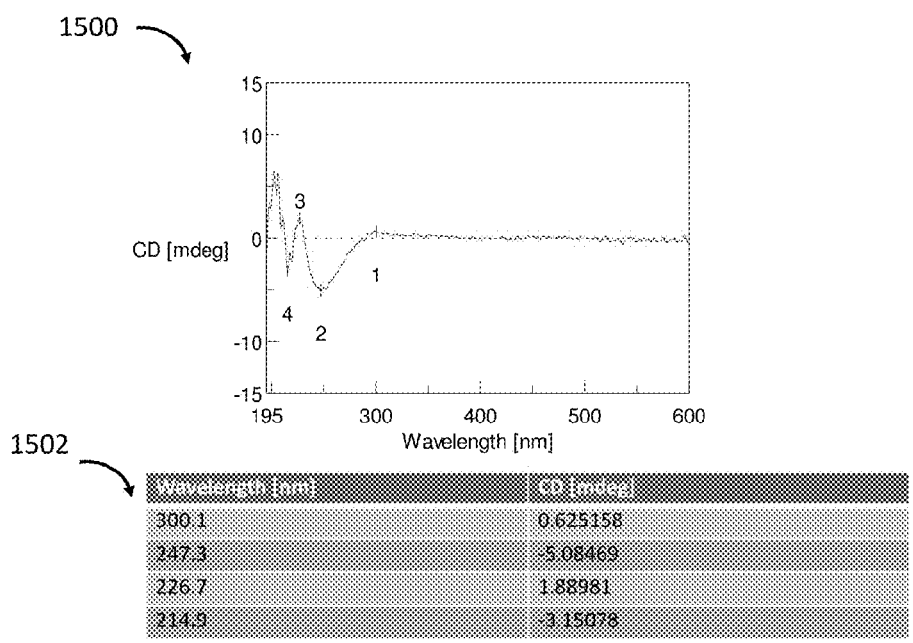
FIG. 15 shows a circular dichroism (CD) spectrum of Sativamide A in CH$_3$OH in accordance with an example embodiment.

In one example embodiment, FIG. 14 shows an UV spectrum 1400 of the Sativamide A. Table 1402 shows UV absorbance data of the Sativamide A. FIG. 15 shows a circular dichroism (CD) spectrum 1500 of the Sativamide A. Table 1502 show CD data of the Sativamide A.

Figure 3:
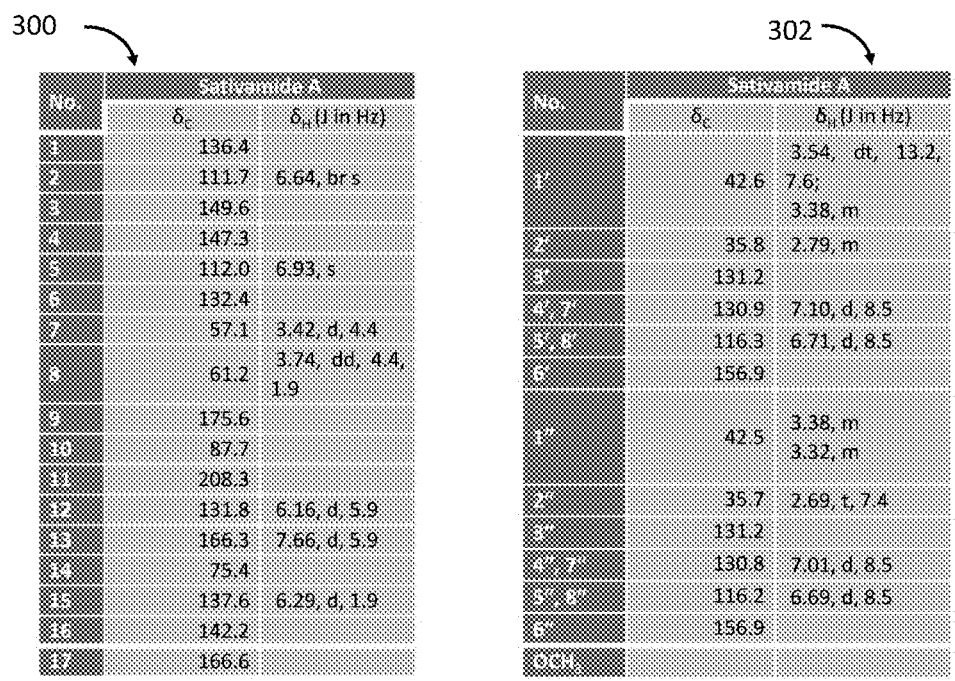
FIG. 3 shows tables that provide $^1$H and $^{13}$C nuclear magnetic resonance (NMR) data of Sativamide A in accordance with an example embodiment.
Figure 18:
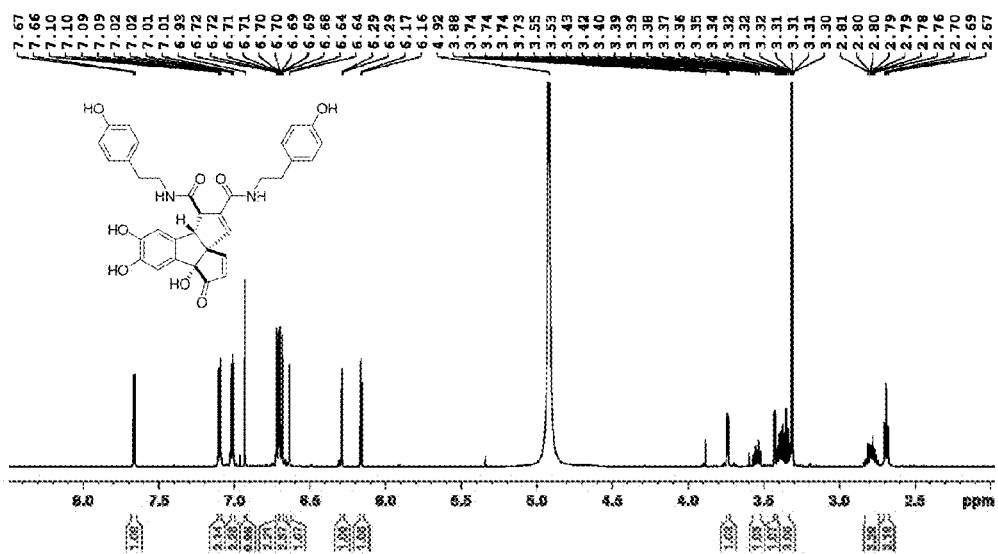
FIG. 18 shows a $^1$H NMR spectrum of Sativamide A in CD$_3$OD in accordance with an example embodiment.
Figure 19:
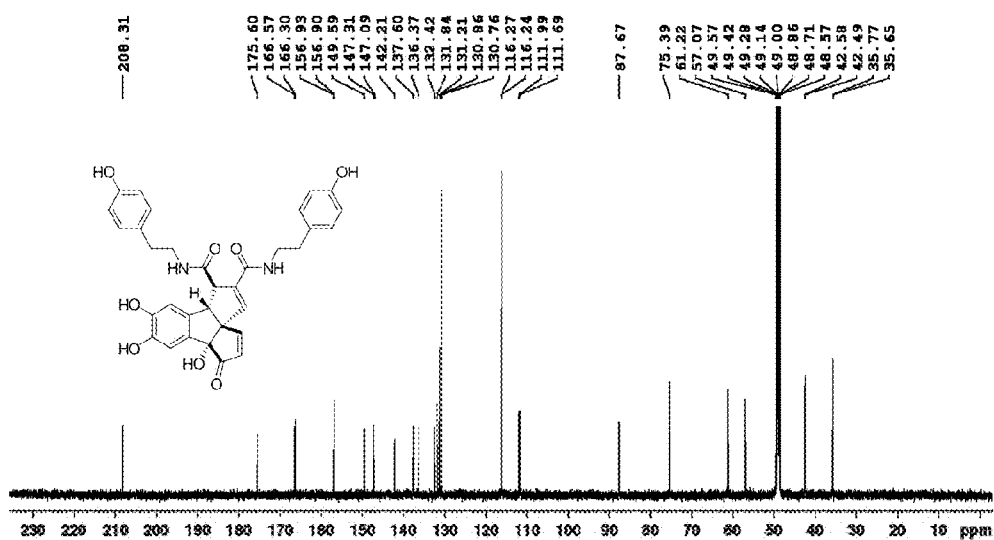
FIG. 19 shows a $^{13}$C NMR spectrum of Sativamide A in CD$_3$OD in accordance with an example embodiment.
Figure 20:
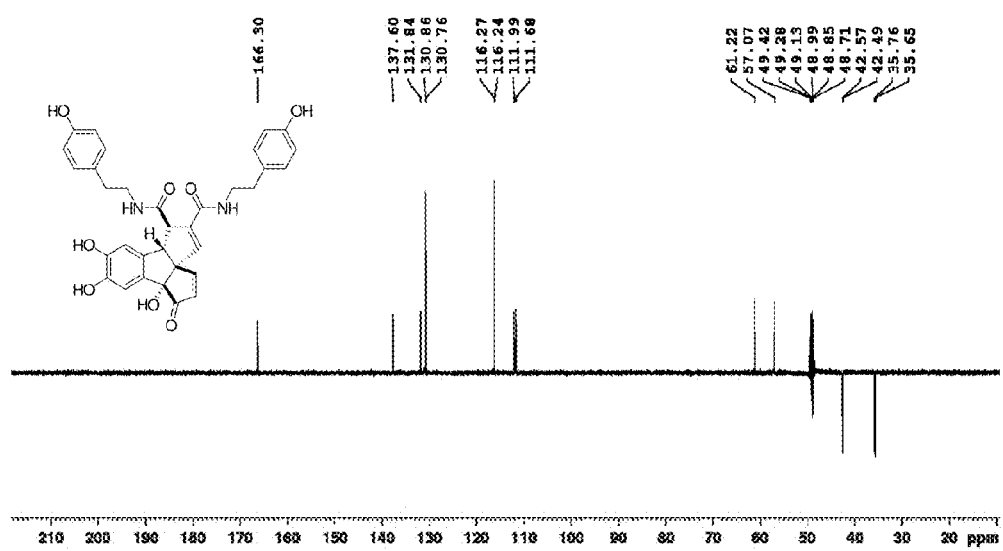
FIG. 20 shows a distortionless enhancement by polarization transfer (DEPT)-135 spectrum of Sativamide A in CD$_3$OD in accordance with an example embodiment.
Figure 21:
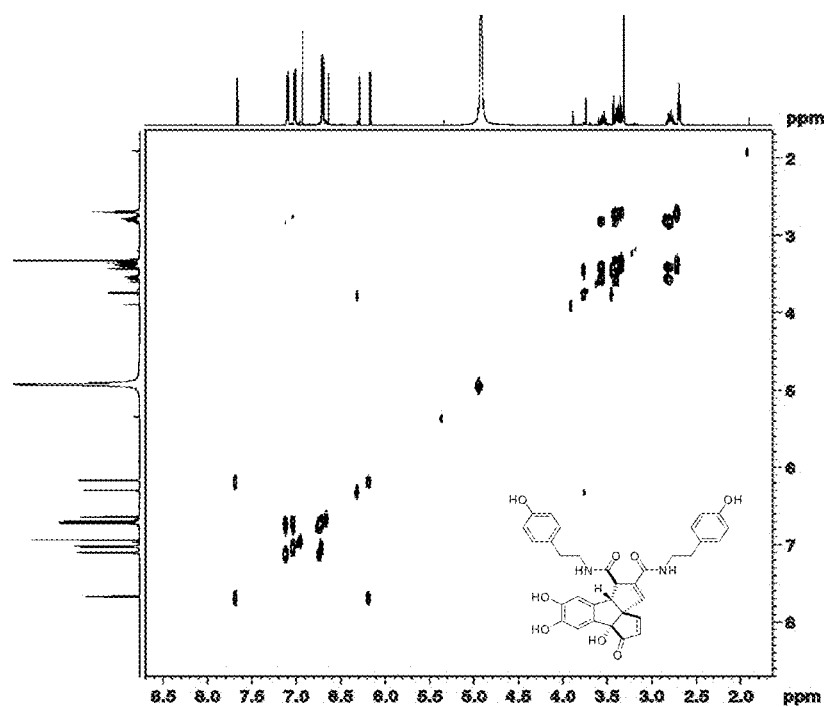
FIG. 21 shows a $^1$H-$^1$H COSY spectrum of Sativamide A in CD$_3$OD in accordance with an example embodiment.
Figure 22:
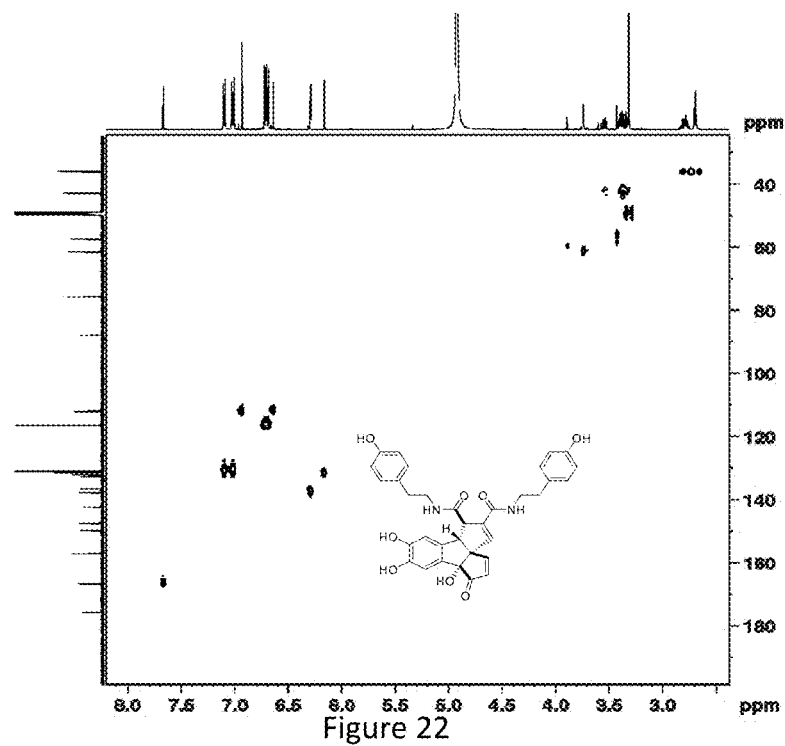
FIG. 22 shows a heteronuclear single quantum coherence (HSQC) spectrum of Sativamide A in CD$_3$OD in accordance with an example embodiment.
Figure 23:
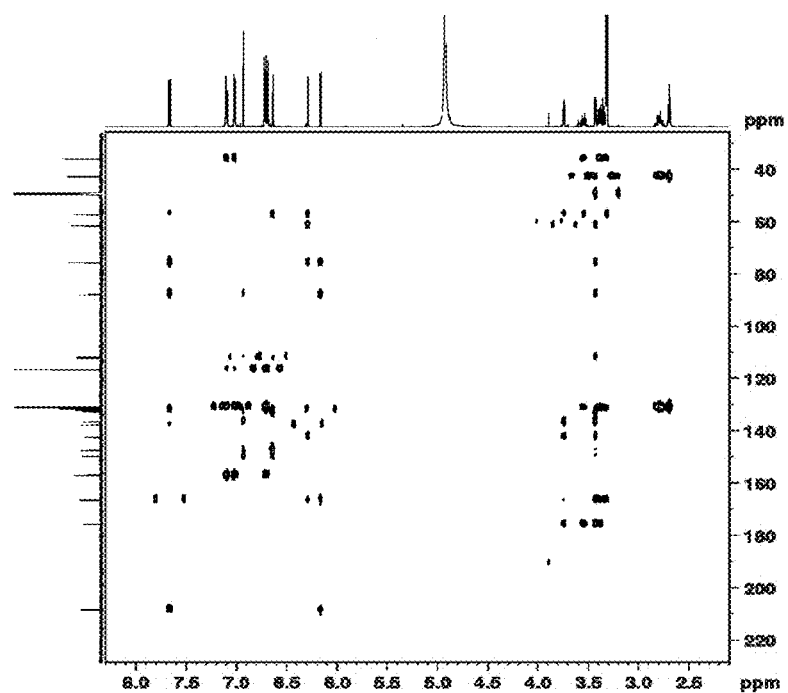
FIG. 23 shows a HMBC spectrum of Sativamide A in CD$_3$OD in accordance with an example embodiment.
Figure 24:
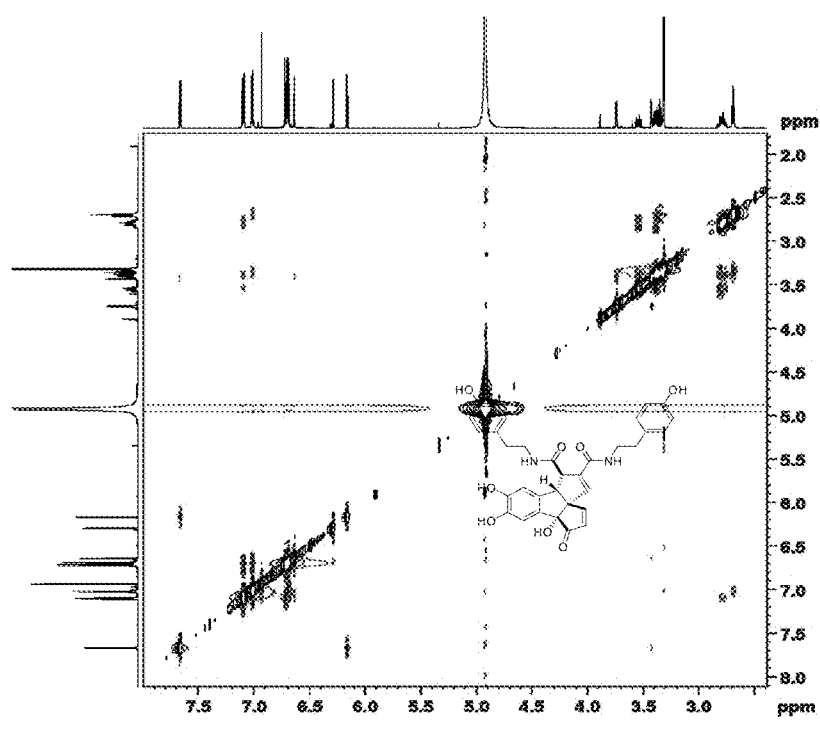
FIG. 24 shows a NOESY spectrum of Sativamide A in CD$_3$OD in accordance with an example embodiment.

In another example embodiment, Tables 300 and 302 in FIG. 3 show $^1$H and $^{13}$C NMR data of the Sativamide A, in which resonances assignable to two p-tyramine moieties (C-1'-C-8' and C-1"-C-8") are demonstrated. These two p-tyramine moieties are found in most of the lignanamides. Data shown in Tables 300 and 302 is assigned by a distortionless enhancement by polarization transfer (DEPT) spectrum as shown in FIG. 20, a heteronuclear single quantum coherence (HSQC) spectrum as shown in FIG. 22, a heteronuclear multiple bond correlation (HMBC) spectrum as shown in FIG. 23, a $^1$H-$^1$H correlation spectroscopy (COSY) spectrum as shown in FIG. 21, and a nuclear overhauser effect spectroscopy (NOESY) spectrum as shown in FIG. 24. Besides, two conjugated olefinic protons at $\delta_H$ 6.16 (d, J=5.9 Hz, H-12) and 7.66 (d, J=5.9 Hz, H-13), an olefinic proton with long range J-coupling at $\delta_H$ 6.29 (d, J=1.9 Hz, H-15), two aromatic singlets at $\delta_H$ 6.64 (H-2) and 6.93 (H-2), and tow ortho-coupled methines at $\delta_H$ 3.42 (d, J=4.4 Hz, H-7) and 3.74 (dd, J=4.4, 1.9 Hz, H-8) are observed in a $^1$H NMR spectrum of the Sativamide A as shown in FIG. 18. Except for those that from two sets of p-tyramine moieties, a $^{13}$C NMR spectrum of the Sativamide A as shown in FIG. 19 shows additional 17 carbon signals that include six benzene carbons, four olefinic carbons, a ketone, two carbonyls, two methines, as well as two quaternary carbons. By way of example, upon taking accounts of the HRMS and NMR data, the Sativamide A is a nor-lignanamide derivative that includes a tetrasubstituted benzene unit, an α,β-unsaturated ketone group, a carbonyl group and an α,β-unsaturated carbonyl group in the skeleton of Sativamide A. The above functional groups and the two p-tyramine moieties occupy 17 degrees of unsaturation, indicating that the skeleton of the Sativamide A possesses a tetracyclic ring system that includes a benzene ring.

FIG. 4A shows the HMBC correlations and the $^1$H-$^1$H COSY correlation of the Sativamide A. The HMBC correlations between H-7 and C-2/C-6, between H-2 and C-6/C-7, and between H-5 and C-10/C-1 suggests that a methine group at $\delta_C$ 57.1 (C-7) and an oxygenated quaternary carbon at $\delta_C$ 87.7 (C-10) are connected to the benzene ring at C-1 and C-6, respectively. The $^1$H-$^1$H COSY correlation between H-7 and H-8, as well as the HMBC correlations between H-7 and C-1/C-9, and between H-8 and C-1 allow to an assignment of C-7-C-8-C-9 chain. The α,β-unsaturated carbonyl group is assigned at C-8 position on the basis of the HMBC correlations between H-7 and C-16, and between H-8 and C-15/C-17. Furthermore, the HMBC correlations between H-12 and C-10 fixes the α,β-unsaturated ketone group at C-10. As a result, a structural fragment of the Sativamide A is determined as shown in FIG. 4B. The last quaternary carbon at $\delta_C$ 75.5 (C-14) is assigned at a center of B, C and D rings of the Sativamide A, as shown in FIG. 1A, which forms an angularly fused triquinane that shares a common vertex (C-14) and two fusion bonds (C-10-C-14 and C-7-C-14). These connections are confirmed by the HMBC correlations between H-8/H-12 and C-14, between H-13 and C-10, between H-13 and C-15, as well as between H-15 and C-7. Further, the HMBC correlations between H-1' and C-9, between H-1" and C-17 places the p-tyramine at C-9 and C-17, respectively. In one example embodiment, a plain structure of the Sativamide A is established as shown in FIG. 1A.

In one example embodiment, a relative configuration of the Sativamide A is determined by a NOESY experiment and the coupling constant value of protons. As shown in FIG. 5, the nuclear overhauser effect (NOE) correlations between H-7 and H-13 indicate that H-7 and C ring are above the A ring and B ring, and assigned as a β-orientation. The coupling constant (J=4.4 Hz) of H-7 and H-8 suggests that H-7 and H-8 are located on the opposite side.

In another example embodiment, to establish an absolute configuration of the Sativamide A, electronic circular dichroism (ECD) curves for the two possible isomers, namely a first isomer and a second isomer, are calculated using the time-dependent density functional theory (TD-DFT) method. By way of example, the first isomer includes chiral carbons at C-7, C-8, C-10 and C-14 with an absolute configuration of 7R, 8R, 10S, 14S. The second isomer includes chiral carbons at C-7, C-8, C-10 and C-14 with an absolute configuration of 7S, 8S, 10R, 14R. In theoretical calculations, the geometry of the molecules is optimized with Gaussian 09 package1 at B3LYP/6-31G (d) computational level. The minimum nature of the structure is confirmed by frequency calculations at the same computational level. Then ECD calculations are carried out in the methanol solvent medium using TD-DFT with B3LYP functional and DGDZVP basis set. FIG. 6 shows the calculated ECD curves of two possible isomers are calculated in which a first isomer 7R, 8R, 10S, 14S is represented by a red line and a second isomer 7S, 8R, 10R, 14R is represented by a blue line. As observed from FIG. 6, the first isomer is in good agreement with an experimental CD spectrum that is represented by a black line. Thus, in one example embodiment, the absolute configuration of chiral carbons of the Sativamide A is determined as 7R, 8R, 10S, 14S.

Figure 8:
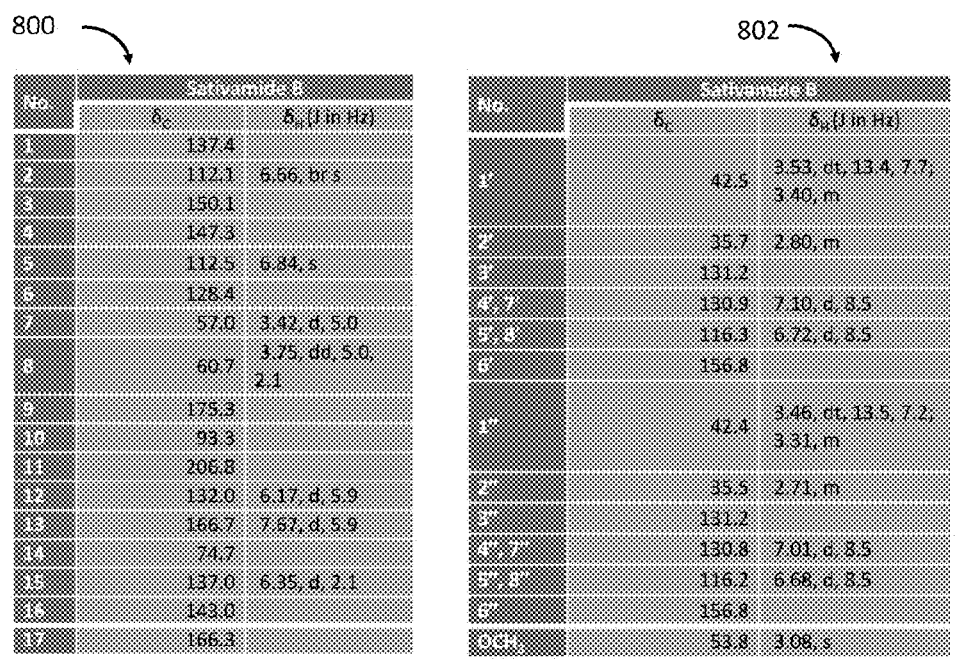
FIG. 8 shows tables that provide $^1$H and $^{13}$C nuclear magnetic resonance (NMR) data of Sativamide B in accordance with an example embodiment.
Figure 28:
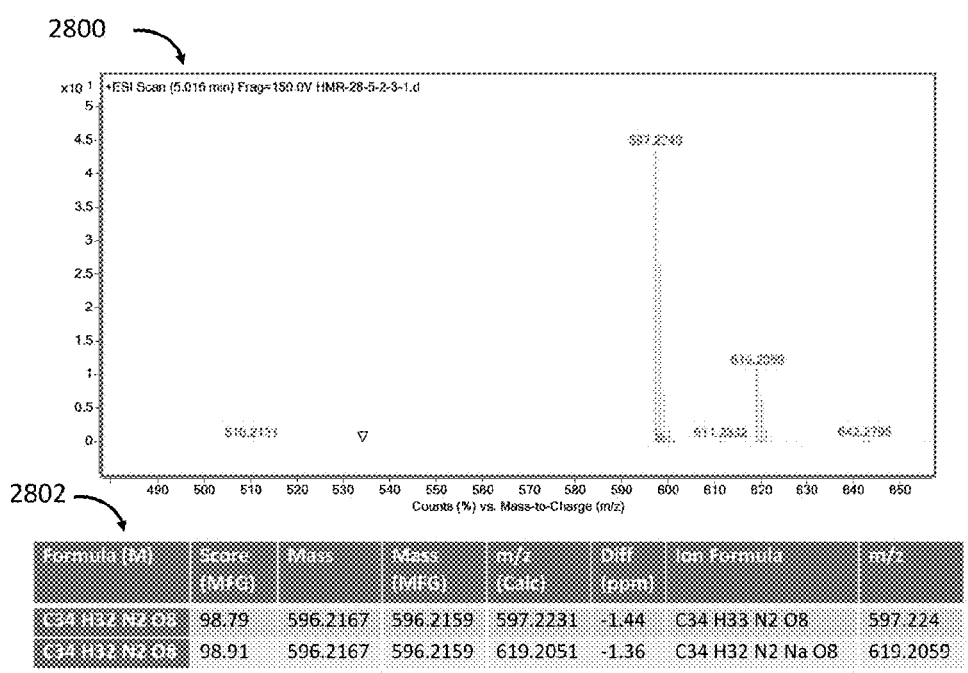
FIG. 28 shows a HR-ESI-MS spectrum of Sativamide B in accordance with an example embodiment.
Figure 29:
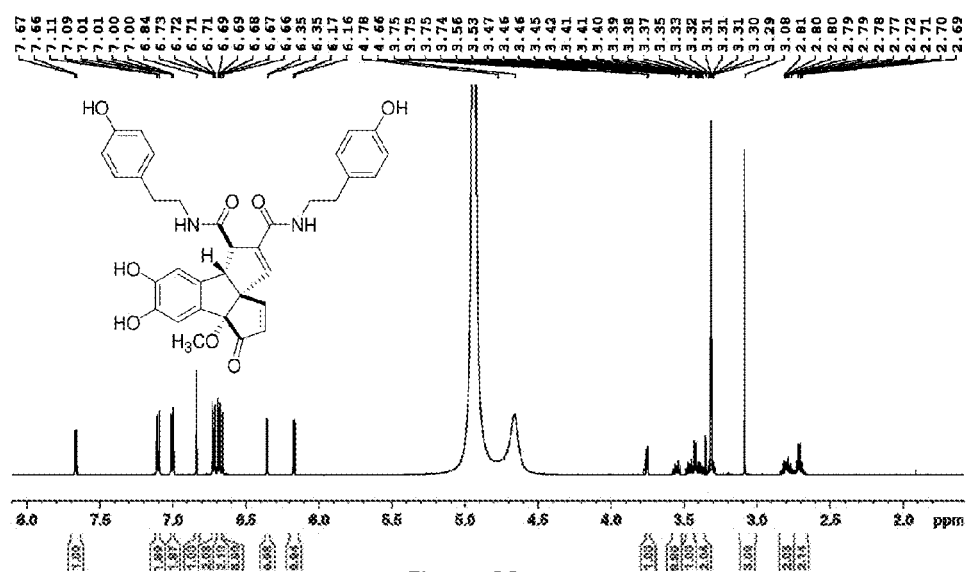
FIG. 29 shows a $^1$H NMR spectrum of Sativamide B in CD$_3$OD in accordance with an example embodiment.
Figure 30:
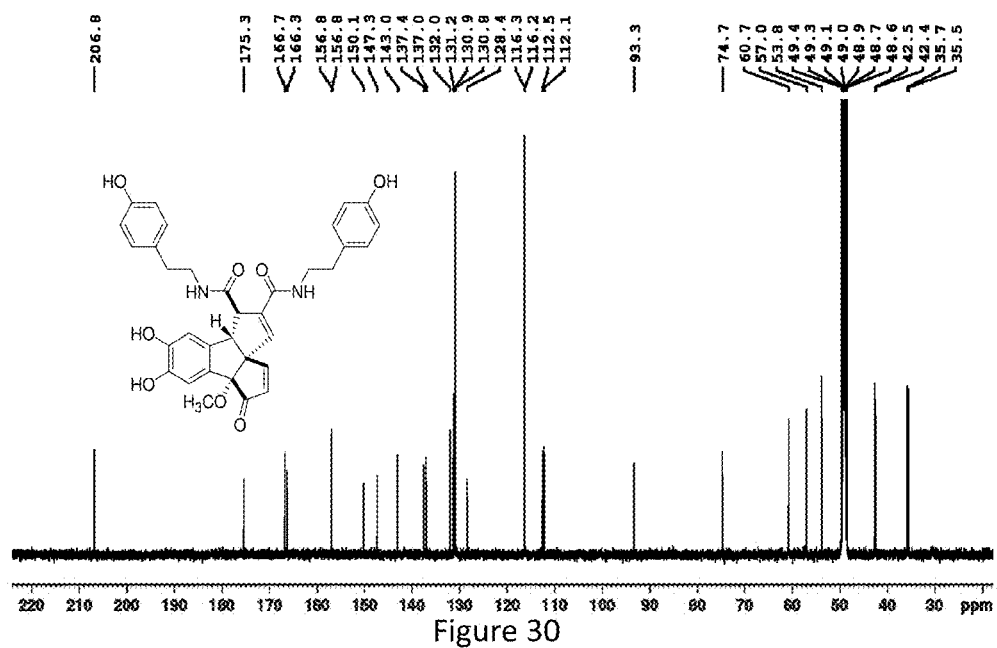
FIG. 30 shows a $^{13}$C NMR spectrum of Sativamide B in CD$_3$OD in accordance with an example embodiment.

In another example embodiment, the Sativamide B is isolated as a light yellow powder with a molecular formula of $C_{34}H_{32}N_2O_8$ (HR-ESI-MS: m/z 597.2240 [M+H]$^+$, calcd 597.2231). FIG. 28 shows a HR-ESI-MS spectrum 2800 of the Sativamide B. Table 2802 shows HR-ESI-MS data of the Sativamide B. By way of example, Table 700 in FIG. 7 shows physico-chemical constants of the Sativamide B. Tables 800 and 802 in FIG. 8 show the $^1$H and $^{13}$C NMR spectroscopic data of the Sativamide B. FIG. 29 shows a $^1$H NMR spectrum of the Sativamide B. FIG. 30 shows a $^{13}$C NMR spectrum of the Sativamide B. In one example embodiment, the spectroscopic data of the Sativamide B are similar to those of the Sativamide A, except that in the Sativamide B, a methoxy group links to C-10 whereas in the Sativamide A, a hydroxy links to C-10. This difference is confirmed by the additional 14 amu in the HR-ESI-MS, by the downfield shifted carbon signal of C-10 ($\delta_C$ 93.3), and by HMBC correlations between protons of methoxy group ($\delta_H$ 3.08, s) and C-10.

In one example embodiment, FIG. 9 shows the NOESY correlations of the Sativamide B. The NOSEY correlations between protons of methoxy group and H-15, between H-7 and H-13 suggest that the stereochemistry of the Sativamide B is same with that of the Sativamide A, which is confirmed by calculated ECD and CD experiments. FIG. 10 shows the calculated ECD curves of two possible isomers are calculated in which a first isomer 7R, 8R, 10S, 14S is represented by a red line and a second isomer 7S, 8R, 10R, 14R is represented by a blue line. As observed from FIG. 10, the first isomer is in good agreement with an experimental CD spectrum that is represented by a black line. Thus, in one example embodiment, the absolute configuration of chiral carbons of the Sativamide B is determined as 7R, 8R, 10S, 14S, and the structure of the Sativamide B is assigned as 10-methoxyl-sativamide A.

Figure 25:
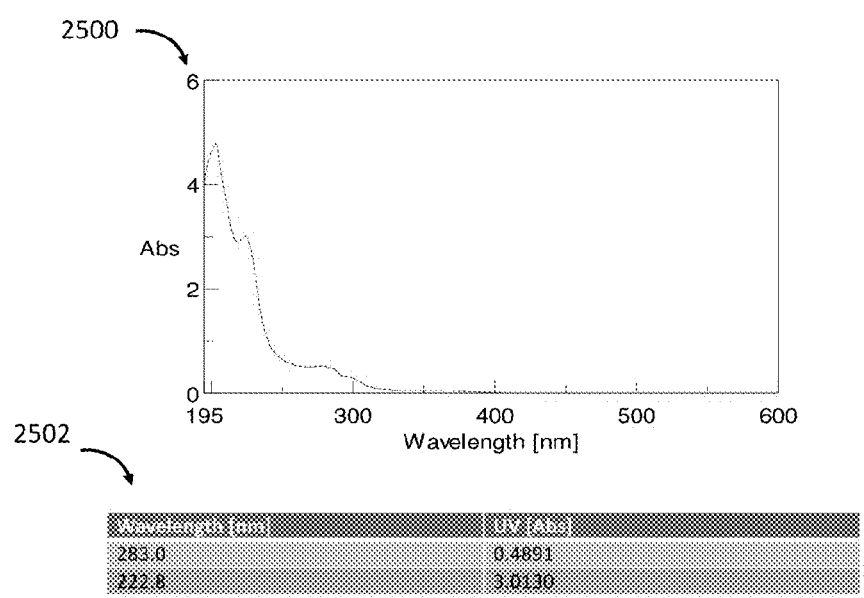
FIG. 25 shows an UV spectrum of Sativamide B in CH$_3$OH in accordance with an example embodiment.
Figure 26:
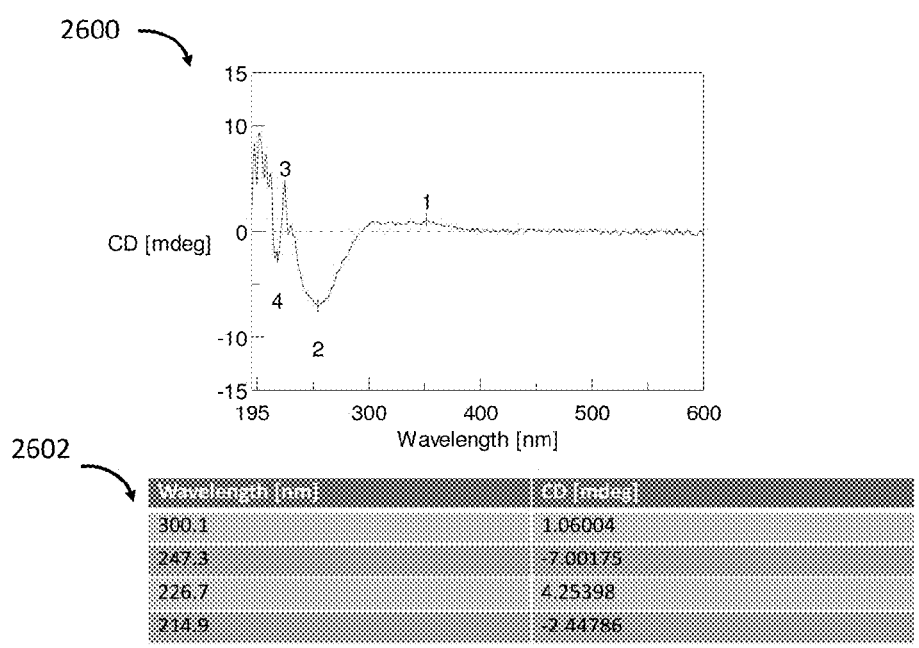
FIG. 26 shows a CD spectrum of Sativamide B in CH$_3$OH in accordance with an example embodiment.
Figure 27:
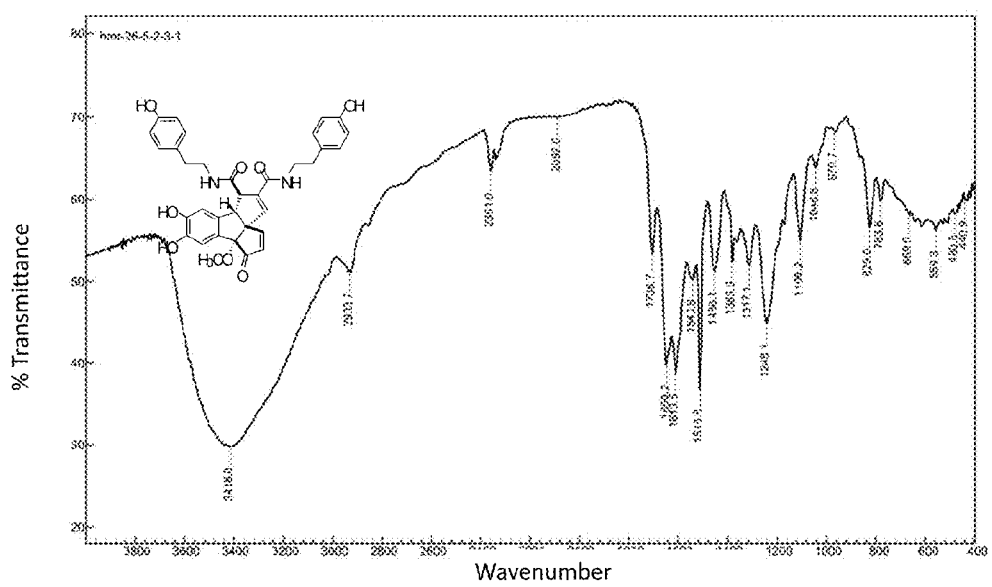
FIG. 27 shows an IR (KBr) spectrum of Sativamide B in accordance with an example embodiment.
Figure 31:
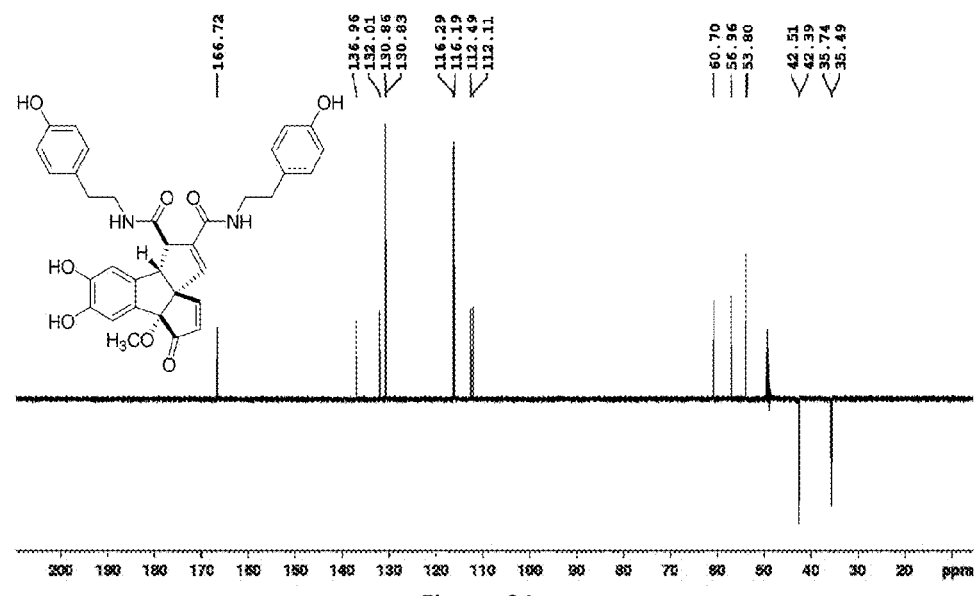
FIG. 31 shows a DEPT-135 spectrum of Sativamide B in CD$_3$OD in accordance with an example embodiment.
Figure 32:
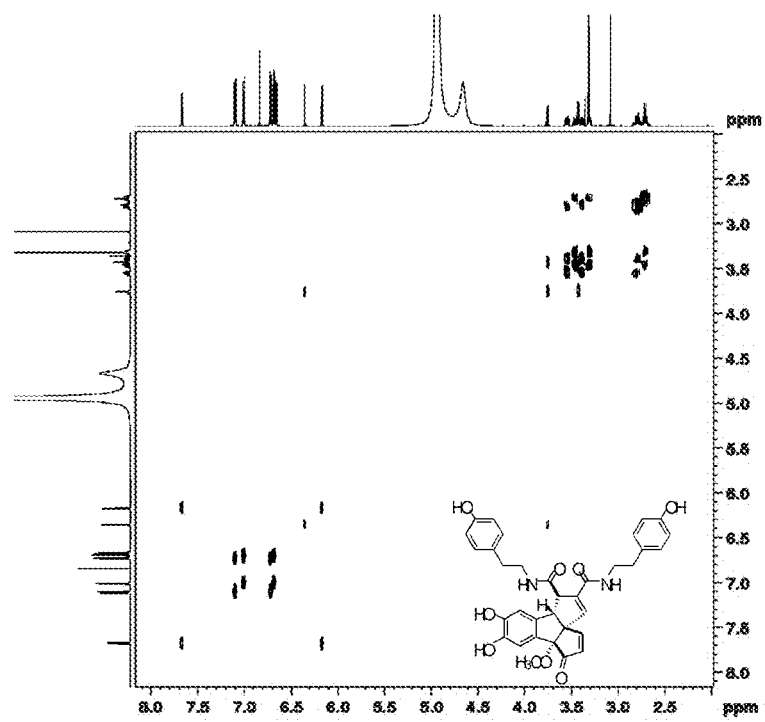
FIG. 32 shows a $^1$H-$^1$H COSY spectrum of Sativamide B in CD$_3$OD in accordance with an example embodiment.
Figure 33:
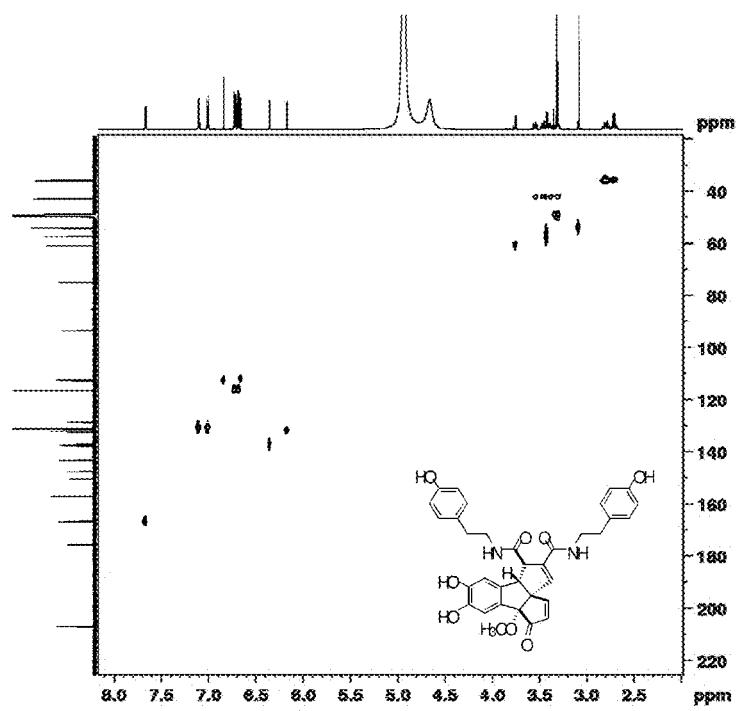
FIG. 33 shows a HSQC spectrum of Sativamide B in CD$_3$OD in accordance with an example embodiment.
Figure 34:
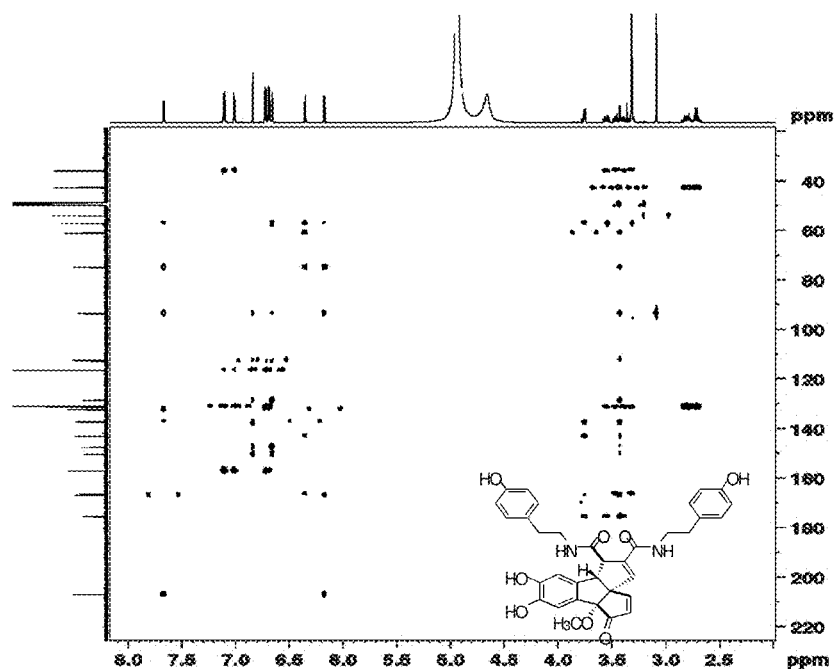
FIG. 34 shows a HMBC spectrum of Sativamide B in CD$_3$OD in accordance with an example embodiment.
Figure 35:
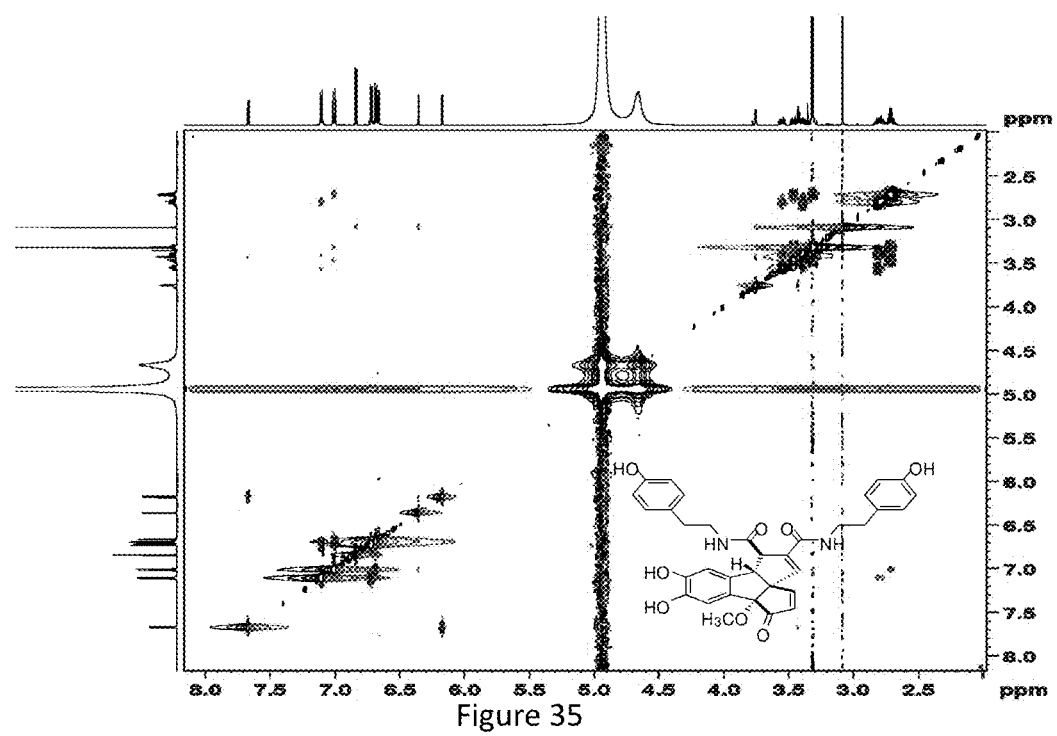
FIG. 35 shows a NOESY spectrum of Sativamide B in CD$_3$OD in accordance with an example embodiment.

In one example embodiment, FIG. 25 shows an UV spectrum 2500 of the Sativamide B. Table 2502 shows UV absorbance data of the Sativamide B. FIG. 26 shows a circular dichroism (CD) spectrum of the Sativamide B. Table 2602 shows CD data of the Sativamide B. FIG. 27 shows an infrared (IR) spectrum of the Sativamide B. FIG. 31 shows a DEPT spectrum of the Sativamide B. FIG. 32 shows a $^1$H-$^1$H COSY spectrum of the Sativamide B. FIG. 33 shows a HSQC spectrum of the Sativamide B. FIG. 34 shows a HMBC spectrum of the Sativamide B. FIG. 35 shows a NOESY spectrum of the Sativamide B.

Figure 11A:
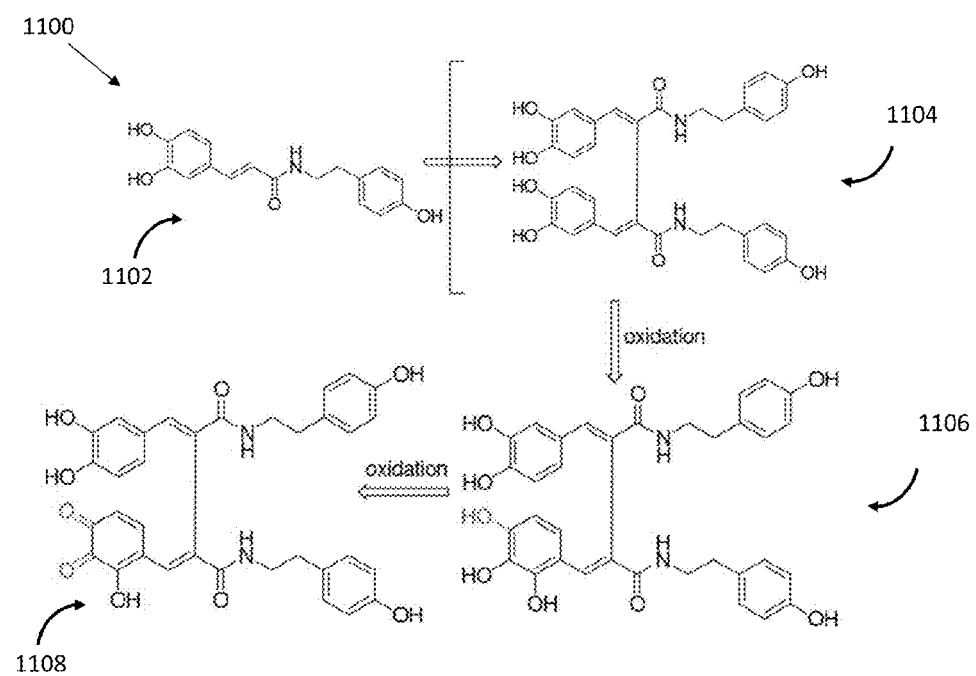
FIGS. 11A and 11B show a biogenetic pathway that synthesizes Sativamide A in accordance with an example embodiment.
Figure 11B:
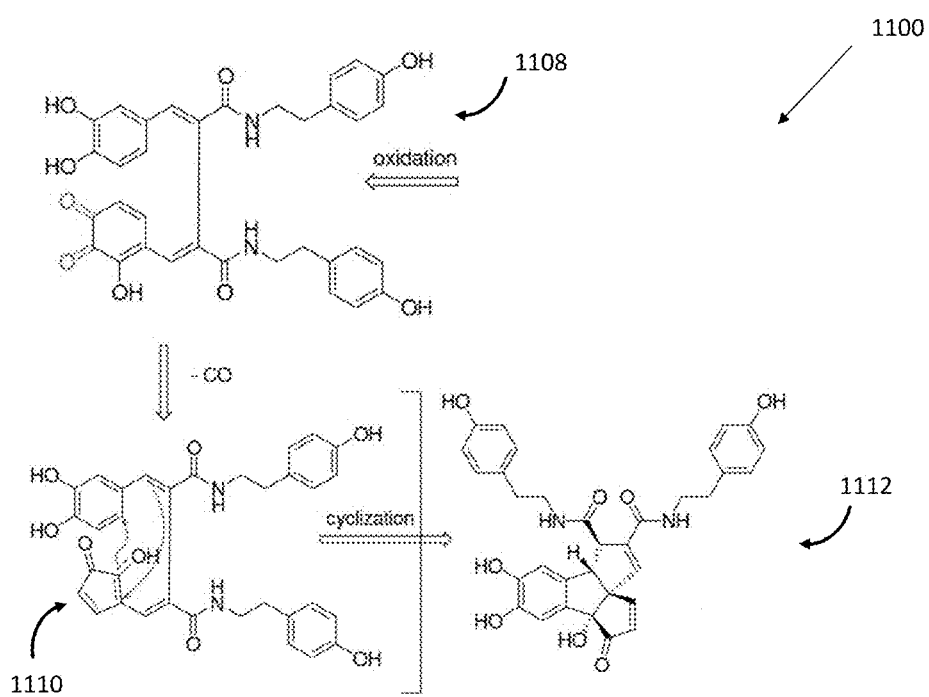

In one example embodiment, the Sativamide A and the Sativamide B represent examples of a class of nor-lignanamides with a benzo-angular triquinane core. In an example embodiment, FIGS. 11A and 11B show a biogenetic pathway 1100 for synthesizing the Sativamide A. Biogenesis of the Sativamide A is derived from N-trans-caffeoyltyramine (Compound 1102), which is isolated as a major amide from the hemp seed. The N-trans-caffeoyltyramine (Compound 1102) is dimerized to form N-trans-caffeoyltyramine dimer (Compound 1104). Subsequently, a series of oxidative reaction are carried out on the N-trans-caffeoyltyramine dimer (Compound 1104) to form an intermediate (Compound 1106) and a hydroxyquinone derivate (Compound 1108). The hydroxyquinone derivate (Compound 1108) is then decarbonylated to form a decarbonylated hydroxyquinone derivate (Compound 1110), which is finally rearranged and cyclized to generate the Sativamide A (Compound 1112).

In one example embodiment, a biogenetic pathway for synthesizing the Sativamide B is similar to the biogenetic pathway 1100 for synthesizing the Sativamide A as shown in FIGS. 11A and 11B.

Endoplasmic reticulum (ER) stress plays an important role in neurodegenerative diseases. Pharmacological targeting of ER stress pathway acts as a therapeutic strategy for several neurodegenerative diseases such as Parkinson's disease and Alzheimer's disease. In an example embodiment, the Sativamide A and the Sativamide B can serve as ER stress modulators.

In one example embodiment, effects of the Sativamide A and the Sativamide B ER stress-induced neurotoxicity on a neuroblastoma cell model (PC12 cells) are tested. PC-12 cells are purchased from the American Type Culture Collection (ATCC). PC-12 cells are cultured in DMEM medium (Invitrogen) supplemented with 100 U/ml penicillin, 100 µg/mL streptomycin, and 10% horse serum and 5% fetal bovine serum (Gibco, Carlsbad, USA). The cells are incubated at 37° C. in a humidified atmosphere of 5% CO2 and 95% air. PC12 cells are seeded into 96-well culture plates ($5.0 \times 10^3$ cells/well) and cultured under standard conditions for 12 h. Cells are then treated with the Sativamide A and the Sativamide B at concentrations of 12.5 µM, 25 µM and 50 µM or a vehicle for another 12 h. After treatment, the whole medium is replaced with fresh medium containing tunicamycin (Tm) (0.1 nM or 1.0 µM) or thapsigargin (Tg) (10 nM or 100 nM) and the cells are incubated for additional 48 h. After incubation, supernatant is changed by fresh medium and thiazolyl blue tetrazolium bromide (MTT) is given at a concentration of 0.5 mg/mL. After incubation at 37° C. for 4 h, the absorbance is measured at 570 nm with a micro-plate reader.

FIG. 12A shows microscopic observations (with magnification of 20×) of PC12 cells that are pre-treated with 50 µM of the Sativamide A and the Sativamide B, in which cell death and cell growth induced by Tm, which is a chemical inducer of ER stress, are markedly reduced. As illustrated in FIG. 12B, the MTT assay shows that the Sativamide A and the Sativamide B mitigate the Tm-induced PC12 cell toxicity in a dose-dependent manner. Cytoprotection by 50 µM of the Sativamide A or the Sativamide B is similar to that by 25 µM of salubrinal (Sal), which is an inhibitor of ER stress and serves as a positive control. As shown in FIG. 12C, the Sativamide A and the Sativamide B also suppress ER stress-mediated cytotoxicity in PC12 cells that is induced by Tg in a dose-dependent manner. Results as shown in FIGS. 12A to 12C indicate that the Sativamide A and the Sativamide B have no adverse effects on cell viability at final concentrations of 50 µM.

In one example embodiment, effects of the Sativamide A and the Sativamide B on ER stress-induced neurotoxicity on a neuroblastoma cell models (SH-SY5Y cells) are tested. SH-SY5Y cells are purchased from the American Type Culture Collection (ATCC). SH-SY5Y cells are cultured in 1:1 mixture of DMEM and F12 medium containing 10% fetal bovine serum (Gibco, Carlsbad, USA). SH-SY5Y cells are incubated at 37° C. in a humidified atmosphere of 5% CO2 and 95% air. SH-SY5Y cells are seeded into 96-well culture plates ($5.0 \times 10^3$ cells/well) and cultured under standard conditions for 12 h. Cells are then treated with the Sativamide A and the Sativamide B at concentrations of 12.5 µM, 25 µM and 50 µM or a vehicle for another 12 h. After treatment, the whole medium is replaced with fresh medium containing Tm (0.1 or 1.0 µM) or Tg (10 or 100 nM) and cells are incubated for additional 48 h. After incubation, supernatant is changed by fresh medium and MTT is given at a concentration of 0.5 mg/mL. After incubation at 37° C. for 4 h, the absorbance is measured at 570 nm with a micro-plate reader.

FIG. 13A shows microscopic observations (with magnification of 20×) of SH-SY5Y cells that are pre-treated with 50 µM of the Sativamide A and the Sativamide B, in which Tg-induced cell death and cell growth are markedly reduced. As illustrated in FIG. 13B, MTT assay shows that the Sativamide A and the Sativamide B mitigate the Tg-induced SH-SY5Y cell toxicity in a dose-dependent manner. Cytoprotection by 50 µM of the Sativamide A or the Sativamide B is similar to that by 25 µM of Sal. As shown in FIG. 13C, the Sativamide A and the Sativamide B also suppress ER stress-mediated Tg-induced cytotoxicity in SH-SY5Y cells tin a dose-dependent manner. Results as shown in FIGS. 13A to 13C indicate that the Sativamide A and the Sativamide B have no adverse effects on cell viability at final concentrations of 50 µM.

In an example embodiment, results shown in FIGS. 12A to 12C and 13A to 13C indicate that the Sativamide A and the Sativamide B have the ability to mitigate the ER stress-induced neurotoxicity. Therefore, in another example embodiment, the Sativamide A and the Sativamide B can be developed as a class of ER-stress inhibitor and neuroprotective agent.

Figure 36A:
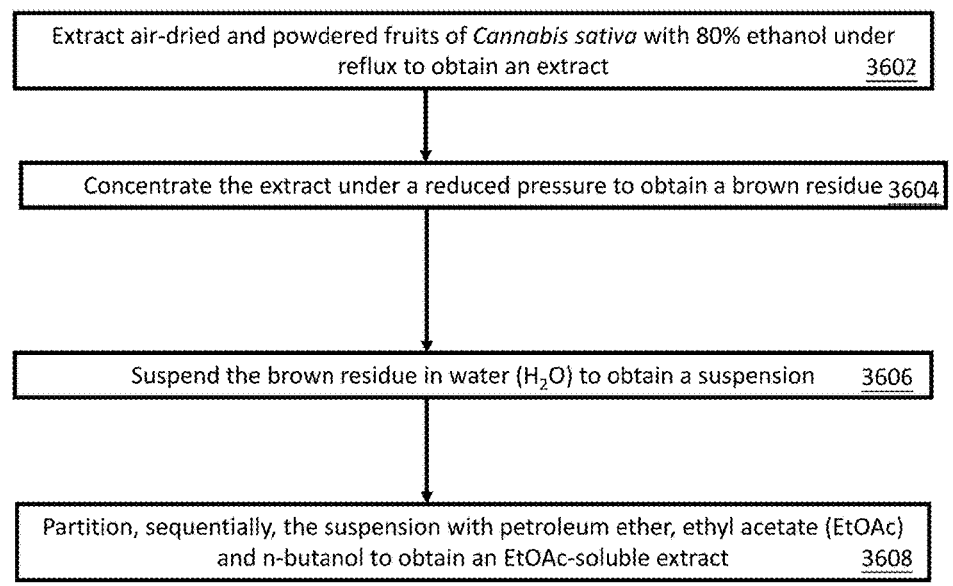
FIGS. 36A and 36B shows a method of isolating a lignanamide from *Cannabis sativa* in accordance with an example embodiment.
Figure 36B:
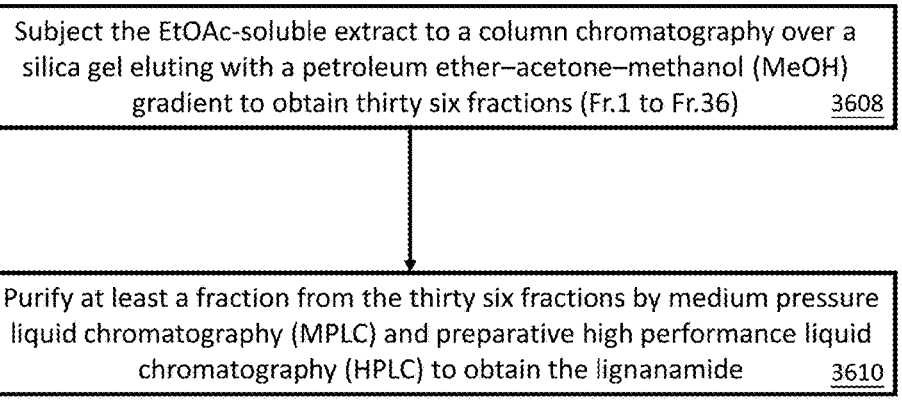

FIGS. 36A and 36B show a method of isolating a lignanamide from *Cannabis sativa*. Air-dried and powdered fruits of *Cannabis sativa* is extracted with 80% ethanol under reflux to obtain an extract in box 3600. The extract is concentrated under a reduced pressure to obtain a brown residue in box 3602. The brown residue is suspended in water ($H_2O$) to obtain a suspension in box 3604. The suspension is sequentially partitioned with petroleum ether, ethyl acetate (EtOAc) and n-butanol to obtain an EtOAc-soluble extract in box 3606. The EtOAc-soluble extract is subject to a column chromatography over a silica gel eluting with a petroleum ether-acetone-methanol (MeOH) gradient to obtain thirty six fractions (Fr.1 to Fr.36) in box 3608. At least a fraction from the thirty six fractions is purified by medium pressure liquid chromatography (MPLC) and preparative high performance liquid chromatography (HPLC) to obtain the lignanamide in box 3610. By way of example, the lignanamide is represented by formula (I) and any derivative of the formula (I), in which R is represented by —OH or —OCH3.

Figure 37:
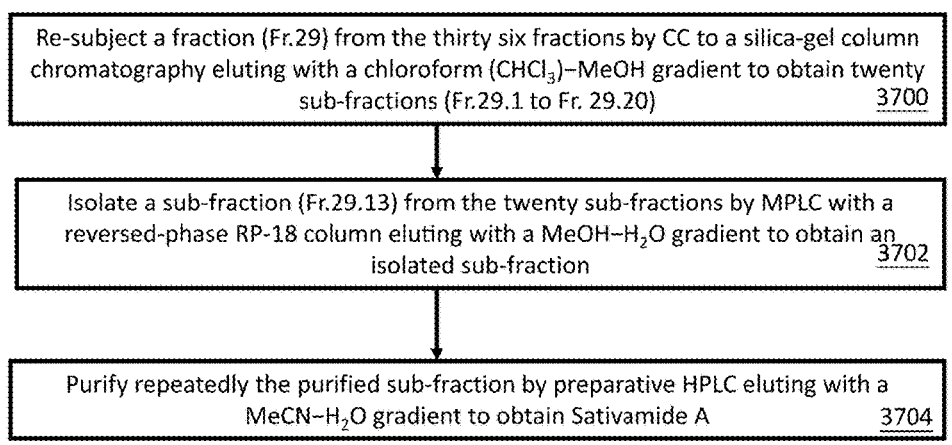
FIG. 37 shows a method of obtaining Sativamide A in accordance with an example embodiment.

FIG. 37 shows a method of obtaining Sativamide A. A fraction (Fr.29) from the thirty six fractions by CC is re-subjected to a silica-gel column chromatography eluting with a chloroform (CHCl₃)-MeOH gradient to obtain twenty sub-fractions (Fr.29.1 to Fr. 29.20) in box 3700. A sub-fraction (Fr.29.13) from the twenty sub-fractions is isolated from the twenty sub-fractions by MPLC with a reversed-phase RP-18 column eluting with a MeOH—H₂O gradient to obtain an isolated sub-fraction in box 3702. The purified sub-fraction is repeatedly purified by preparative HPLC eluting with a MeCN—H₂O gradient to obtain the Sativamide A in box 3704.

Figure 38:
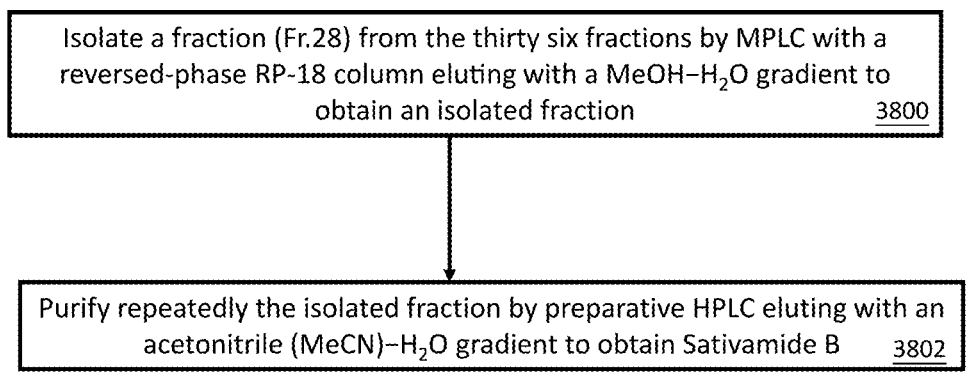
FIG. 38 shows a method of obtaining Sativamide B in accordance with an example embodiment.

FIG. 38 shows a method of obtaining Sativamide B. A first fraction (Fr.28) from the thirty six fractions is isolated from the thirty six fractions by MPLC with a reversed-phase RP-18 column eluting with a MeOH—H₂O gradient to obtain an isolated fraction in box 3800. The isolated fraction is repeatedly purified by preparative HPLC eluting with an acetonitrile (MeCN)—H₂O gradient to obtain the Sativamide B in box 3802.

What is claimed is:

1. A method of treating neurodegenerative disease in a person in need thereof, comprising:
   administering a therapeutically effective amount of a lignanamide to the person to treat the neurodegenerative disease;
   wherein the lignanamide includes a benzo-angular triquinane skeleton, and the lignanamide is represented by formula (I);

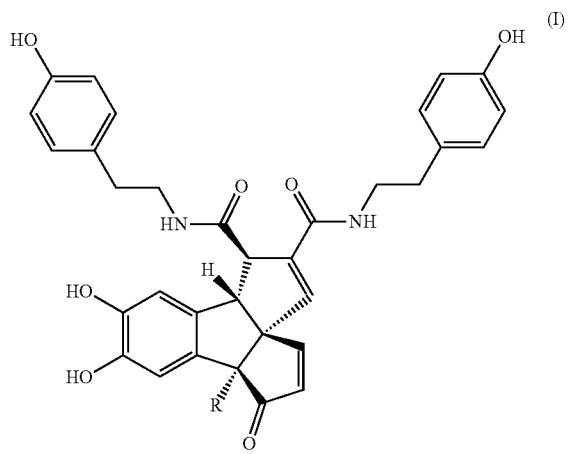

wherein R is represented by —OH or —OCH₃,
   wherein the neurodegenerative disease is selected from a group consisting of neuroblastoma, pheochromocytoma, Parkinson's disease (PD), Alzheimer's disease (AD), Huntington's disease (HD), and prion diseases.

2. The method of claim 1, wherein the neurodegenerative disease is induced by an endoplasmic reticulum (ER) stress.

3. The method of claim 1, wherein when R is represented by —OH in the formula (I), the lignanamide is Sativamide A and represented by a chemical formula of $C_{33}H_{30}N_2O_8$.

4. The method of claim 1, wherein when R is represented by —OCH₃ in the formula (I), the lignanamide is Sativamide B and represented by a chemical formula of $C_{34}H_{32}N_2O_8$.

* * * * *